United States Patent [19]

Minokami et al.

[11] Patent Number: 5,686,398
[45] Date of Patent: Nov. 11, 1997

[54] ADDITIVE FOR LUBRICANT OR FUEL, LUBRICATING OIL COMPOSITION OR FUEL COMPOSITION CONTAINING IT, AND SUBSTITUTED HYDROXYAROMATIC ESTER DERIVATIVE

[75] Inventors: Tomiyasu Minokami; Hiroaki Koshima; Harutomo Ikeda, all of Sodegaura; Masahisa Gotoh, Ichihara, all of Japan

[73] Assignee: Idemitsu Kosan Co., Ltd., Tokyo, Japan

[21] Appl. No.: 557,103

[22] PCT Filed: Jun. 10, 1994

[86] PCT No.: PCT/JP94/00944

§ 371 Date: Dec. 6, 1995

§ 102(e) Date: Dec. 6, 1995

[87] PCT Pub. No.: WO94/29264

PCT Pub. Date: Dec. 22, 1994

[30] Foreign Application Priority Data

| Jun. 15, 1993 | [JP] | Japan | 5-143532 |
| Sep. 30, 1993 | [JP] | Japan | 5-244353 |
| Mar. 30, 1994 | [JP] | Japan | 6-061260 |

[51] Int. Cl.$^6$ ............................. C10M 129/68; C10L 1/18
[52] U.S. Cl. ............................. 508/481; 508/480; 508/483; 508/502; 44/389; 44/400; 560/56; 560/64; 560/67; 560/73
[58] Field of Search ............................. 508/502, 480, 508/481, 483; 44/389, 400

[56] References Cited

U.S. PATENT DOCUMENTS 2,580,038  12/1951  Mikeska ............................. 508/480

(List continued on next page.)

FOREIGN PATENT DOCUMENTS 19 36 280  1/1970  Germany .

OTHER PUBLICATIONS

Smalheer et al, "Lubricant Additives", pp. 1–11, 1967.

(List continued on next page.)

*Primary Examiner*—Ellen M. McAvoy
*Attorney, Agent, or Firm*—Antonelli, Terry, Stout & Kraus, LLP.

[57] ABSTRACT

There are herein disclosed an additive for a lubricant or a fuel which comprises at least one selected from the group consisting of substituted hydroxyaromatic ester derivatives represented by the general formulae (I) and (II)

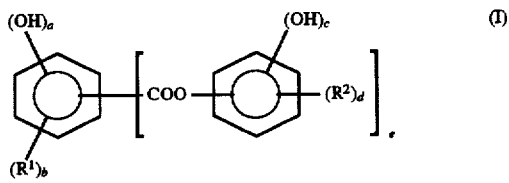

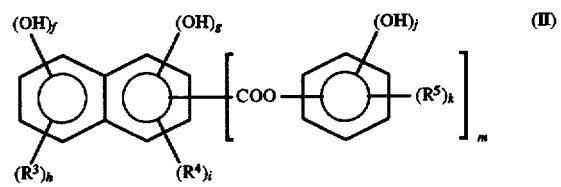

wherein $R^1$ to $R^5$ are each an organic group having 6 or more carbon atoms, a, b, d, e, k and m are from 1 to 3, c, f, g, i and j are from 0 to 3, and h is from 0 to 4, but (f+g) is from 1 to 3, and (h+i) is from 1 to 6, an additive composition for a lubricant or a fuel, and a lubricating oil composition or a fuel composition containing the above-mentioned additive.

The above-mentioned additive for the lubricant or the fuel is desirable as an ashless detergent excellent in high-temperature stability in place of a metal detergent, and the lubricating oil composition or the fuel composition containing this additive can suitably be used as the lubricant or the fuel for an internal combustion engine which can comply with future exhaust gas controls.

34 Claims, 14 Drawing Sheets

U.S. PATENT DOCUMENTS

| | | | |
|---|---|---|---|
| 2,936,320 | 5/1960 | Benoit, Jr. | 508/480 |
| 3,021,357 | 2/1962 | Swakon | 508/480 |
| 3,282,842 | 11/1966 | Bonner et al. | 508/502 |
| 3,470,099 | 9/1969 | Burkard et al. | 508/483 |
| 3,591,553 | 7/1971 | Lappin et al. | 524/291 |
| 3,884,960 | 5/1975 | Spivack et al. | 44/389 |
| 3,890,301 | 6/1975 | Piasek et al. | 508/481 |
| 4,172,802 | 10/1979 | Rieder | 508/481 |
| 5,164,122 | 11/1992 | Lange et al. | 508/481 |
| 5,599,359 | 2/1997 | Cherpeck | 44/389 |

OTHER PUBLICATIONS

Journal Of The Indian Chemical Society, vol. 12, 1935, Calcutta, India; pp. 231–236; P. Parameswaren Pillay: "On Anacardic Acid. Part II. The Constitution Of Tetrahydronacardic Acid".

FIG. I

ADDITIVE FOR LUBRICANT OR FUEL, LUBRICATING OIL COMPOSITION OR FUEL COMPOSITION CONTAINING IT, AND SUBSTITUTED HYDROXYAROMATIC ESTER DERIVATIVE

TECHNICAL FIELD

The present invention relates to an additive for a lubricant or a fuel, an additive composition for the lubricant or the fuel, a lubricating oil composition or a fuel composition containing the additive for the lubricant or the fuel, a novel substituted hydroxyaromatic ester derivative, and a process for preparing the derivative. More specifically, the present invention relates to an additive for a lubricant useful as an excellent ashless detergent and an anti-wear agent, an additive composition for the lubricant excellent in high-temperature stability and the dispersibility of fine particles which can be used in an engine oil, particularly a diesel engine oil and a methanol engine oil compliable with future severe exhaust gas controls, and a lubricating oil composition containing the above-mentioned additive for the lubricant. Furthermore, the present invention relates to an additive for a fuel which is useful as an excellent ashless detergent and is excellent in wear resistance of an injection pump and storage stability to a fuel containing a particulate reducer, an additive composition for a fuel which is excellent in high-temperature stability, has the dispersibility of fine particles, and is useful as an excellent ashless detergent dispersant for a fuel oil, and a fuel composition containing the additive for the fuel. In addition, the present invention also relates to a novel substituted hydroxyaromatic ester derivative which is useful as an ashless detergent having excellent high-temperature stability in place of a conventional metal detergent, and a process for efficiently preparing the derivative.

BACKGROUND ART

Examples of conventional ashless dispersants usually include succinimido-containing dispersants and hydroxybenzylamine (Mannich base)-containing dispersants, and importance has been attached to their remarkable fine particles dispersion function. For this reason, they have been widely used as additives for gasoline and a diesel engine oil. Moreover, it has been confirmed that they can exert a synergistic effect with a zinc dialkyldithiophosphate and a metal detergent, and therefore they have been utilized as the extremely important additives for the lubricant.

In recent years, however, it has often been indicated that these dispersants are poor in high-temperature stability (high-temperature detergency).

A conventional lubricating oil for an internal combustion engine is usually constituted of a base oil, an ashless dispersant such as polybutenylsuccinimide, a metal detergent such as a sulfonate or a phenate of an alkaline earth metal and a wear-resisting agent such as a zinc alkyldithiophosphate, but there has been a problem that oxides and sulfates are produced from metals in the additive components by combustion to cause environmental pollution.

Nowadays, in an internal combustion engine, particularly a diesel engine, measures against the environmental pollution attributable to particulates, $NO_x$ and the like in an exhaust gas are important themes. As these measures, exhaust gas purifying devices such as a particulate trap and an $NO_x$ removing catalyst have been used, but a conventional lubricating oil for the internal combustion engine is accompanied with a problem of clogging by metal oxides and sulfides produced during combustion. Therefore, a lubricant for the internal combustion engine has been required which permits minimizing the exhaust of these metal oxides and sulfides.

Furthermore, as one resolution of the future measures against the exhaust gas, much attention has been paid to a methanol engine. In the diesel engine, a gas oil is injected into the engine by an injection pump, but lubrication in the pump is self-lubrication by the gas oil itself. On the contrary, in the case of the methanol engine, an engine oil is usually injected into the injection pump, because the lubrication of methanol itself is low. In this case, the compatibility of methanol with the engine oil is poor, so that an additive is deposited in methanol. Particularly in the case that a metal detergent is used, there is a problem that a metallic component such as calcium clogs a nozzle injection opening, and thus, a lubricating oil for the internal combustion engine has been required which permits minimizing the amount of the metallic component.

As such future measures against the exhaust gas, for example, there has been suggested an ash-free lubricating oil composition obtained by mixing a base oil for the lubricating oil with an alkyl(3,5-di-t-butyl-4-hydroxyphenyl) carboxylate, a succinimide-containing ashless dispersant and an ashless antioxidant (Japanese Patent Application Laid-open No. 353598/1992). This composition is however accompanied by a problem that the high-temperature stability (the high-temperature detergency) is not sufficiently satisfactory.

On the other hand, U.S. Pat. No. 4,098,708 has suggested, as dispersants for a lubricating oil and a fuel oil, esters of alkyl-substituted hydroxyaromatic carboxylic acids having at least about 10 carbon atoms and their derivatives. As alcohol components suitable for these esters, monovalent and polyvalent hydrocarbon alcohols are enumerated, and as their typical examples, substituted phenols such as cresol are recited. Also in the case of these esters, however, the high-temperature stability (the high-temperature detergency) is not sufficiently satisfactory.

In the specification of East German Patent No. 268933, there has been suggested a process for preparing an alkylphenol ester of an alkyl-substituted hydroxyaromatic carboxylic acid having 1 to 14 carbon atoms. In examples of this patent, an isobutyl group, an ethylphenyl group and the like are enumerated as typical examples of alkyl groups in the esters.

In addition, CA. Re. No. 19310-46-4 has suggested p-(1,1,3,3-tetramethylbutyl)phenyl 5-(1,1,3,3-tetramethyl-butyl) salicylate esters. However, any substituted hydrocarbon groups having 9 or more carbon atoms are not referred to, and applications as additives for the lubricant or the fuel are not referred to, either.

Moreover, CA. Re. No. 29875-45-4 has suggested 4-hydroxy-bis(p-dodecylphenyl) isophthalate esters. However, in the case of these esters, the aromatic ring of an isophthalic acid is not subjected by any hydrocarbon group.

DISCLOSER OF THE INVENTION

An object of the present invention is to provide an additive for a lubricant as an ash-free detergent and an anti-wear agent (an abrasion-resisting agent) useful to an oil for a diesel engine and an oil for a methanol engine which can comply with future exhaust gas controls, or an additive for a fuel as an ash-free detergent useful to a fuel for an internal combustion engine.

Another object of the present invention is to provide an additive for a fuel which is excellent in the abrasion resistance of an injection pump and the storage stability of a fuel to which a particulate reducer or the like is added.

Still another object of the present invention is to provide an additive composition for a lubricant as an ashless detergent dispersant having excellent high-temperature stability (high-temperature detergency) and a fine particles dispersion function, and a lubricating oil composition containing the additive for the lubricant.

A further object of the present invention is to provide an additive composition for a fuel which has excellent high-temperature stability (high-temperature detergency) and a fine particles dispersion function and which is useful as an ashless detergent dispersant for a fuel, and a fuel composition containing the additive for the fuel.

A still further object of the present invention is to provide a novel substituted hydroxyaromatic ester derivative useful as the additive for the lubricant or the fuel (the ashless detergent), and a process for efficiently preparing this derivative.

The present inventors have repeatedly researched to achieve the above-mentioned objects. As a result, it has been found that an additive for a lubricant containing a specific substituted hydroxyaromatic ester derivative is useful as an excellent ashless detergent and anti-wear agent for a lubricant, and an additive for a fuel containing a specific substituted hydroxyaromatic ester derivative is useful as an excellent ashless detergent for a fuel and is excellent in the abrasion resistance of an injection pump and the storage stability of a fuel to which a particulate reducer or the like is added. Furthermore, it has also been found that, by blending the additive for the lubricant or the fuel (the ashless detergent) with a conventional ashless dispersant, an additive composition for a lubricant or a fuel which is excellent in high-temperature stability (high-temperature detergency) and useful as an ashless detergent dispersant having a fine particles dispersion function can be obtained. In addition, it has also been found that a substituted hydroxyaromatic ester derivative obtained by reacting a specific alkyl group-substituted salicylic acid or a specific hydrocarbon group-substituted hydroxybenzenedicarboxylic acid with a specific phenol is a novel compound useful as an additive for a lubricant or a fuel excellent in high-temperature stability (high-temperature detergency). The present invention has been completed on the basis of these findings.

That is to say, the present invention provides:

(1) An additive for a lubricant comprising at least one selected from the group consisting of substituted hydroxyaromatic ester derivatives represented by the general formula (I)

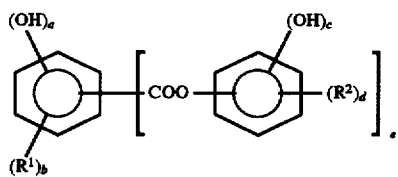

wherein $R^1$ and $R^2$ are each an organic group having 6 or more carbon atoms, and they may be the same or different; a, b, c, d and e are integers satisfying the relations of $1 \leq a \leq 3$, $1 \leq b \leq 3$, $0 \leq c \leq 3$, $1 \leq d \leq 3$, $1 \leq e \leq 3$, $3 \leq (a+b+e) \leq 6$ and $1 \leq (c+d) \leq 5$, respectively; and when a plurality of $R^1$s and $R^2$s are present, they may be the same or different, and the general formula (II)

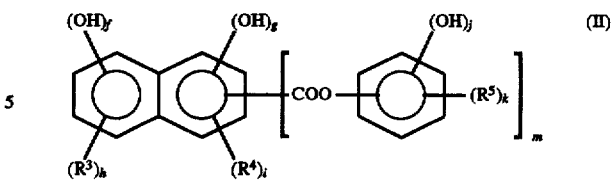

wherein $R^3$, $R^4$ and $R^5$ are each an organic group having 6 or more carbon atoms, and they may be the same or different; f, g, h, i, j, k and m are integers satisfying the relations of $0 \leq f \leq 3$, $0 \leq g \leq 3$, $1 \leq (f+g) \leq 3$, $0 \leq h \leq 4$, $0 \leq i \leq 3$, $1 \leq (h+i) \leq 6$, $0 \leq j \leq 3$, $1 \leq k \leq 3$, $1 \leq m \leq 3$, $3 \leq (f+g+h+i+m) \leq 8$ and $1 \leq (j+K) \leq 5$, respectively; and when a plurality of $R^3$s, $R^4$s and $R^5$s are present, they may be the same or different.

(2) An additive composition for a lubricant which comprises (a) at least one selected from substituted hydroxyaromatic ester derivatives represented by the general formulae (I) and (II), and (b) an ashless dispersant.

(3) A lubricant composition which is obtained by adding, to a base oil for a lubricating oil, at least one selected from substituted hydroxyaromatic ester derivatives represented by the general formulae (I) and (II).

(4) A lubricant composition which is obtained by adding, to a base oil for a lubricant, (a) at least one selected from substituted hydroxyaromatic ester derivatives represented by the general formulae (I) and (II), and (b) an ashless dispersant.

(5) An additive for a fuel which comprises at least one selected from substituted hydroxyaromatic ester derivatives represented by the general formulae (I) and (II)

(6) An additive composition for a fuel which comprises (a) at least one selected from substituted hydroxyaromatic ester derivatives represented by the general formulae (I) and (II), and (b) an ashless dispersant.

(7) A fuel composition which is obtained by adding, to a fuel, at least one selected from substituted hydroxyaromatic ester derivatives represented by the general formulae (I) and (II).

(8) A fuel composition which is obtained by adding, to a fuel, (a) at least one selected from substituted hydroxyaromatic ester derivatives represented by the general formulae (I) and (II), and (b) an ashless dispersant.

(9) A substituted hydroxyaromatic ester derivative represented by the general formula (IV)

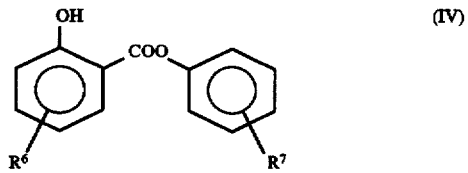

wherein $R^6$ and $R^7$ are each an alkyl group having 9 to 20 carbon atoms, and they may be the same or different.

(10) A process for preparing a substituted hydroxyaromatic ester derivative represented by the general formula (IV) which comprises the step of reacting an alkyl group-substituted salicylic acid represented by the general formula (V)

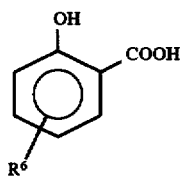

wherein $R^6$ is an alkyl group having 9 to 20 carbon atoms, with an alkyl-substituted phenol represented by the general formula (VI)

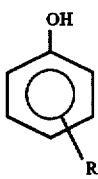

wherein $R^7$ is an alkyl group having 9 to 20 carbon atoms, in the presence of no catalyst or a catalyst.

(11) A substituted hydroxyaromatic ester derivative represented by the general formula (VII)

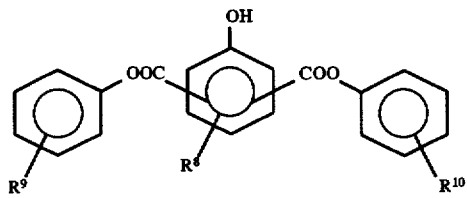

wherein $R^8$, $R^9$ and $R^{10}$ are each a hydrocarbon group, and they may be the same or different.

(12) A process for preparing a substituted hydroxyaromatic ester derivative represented by the general formula (VII) which comprises the step of reacting a hydrocarbon group-substituted hydroxybenzenedicarboxylic acid represented by the general formula (VIII)

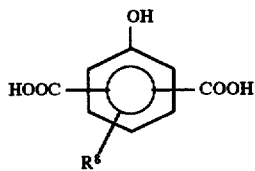

wherein $R^8$ is a hydrocarbon group, with at least one of hydrocarbon group-substituted phenols represented by the general formula (IX)

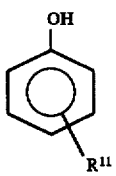

wherein $R^{11}$ is $R^9$ or $R^{10}$, and it is a hydrocarbon group, in the presence of no catalyst or a catalyst.

BEST MODE FOR CARRYING OUT THE INVENTION

Figure 1:
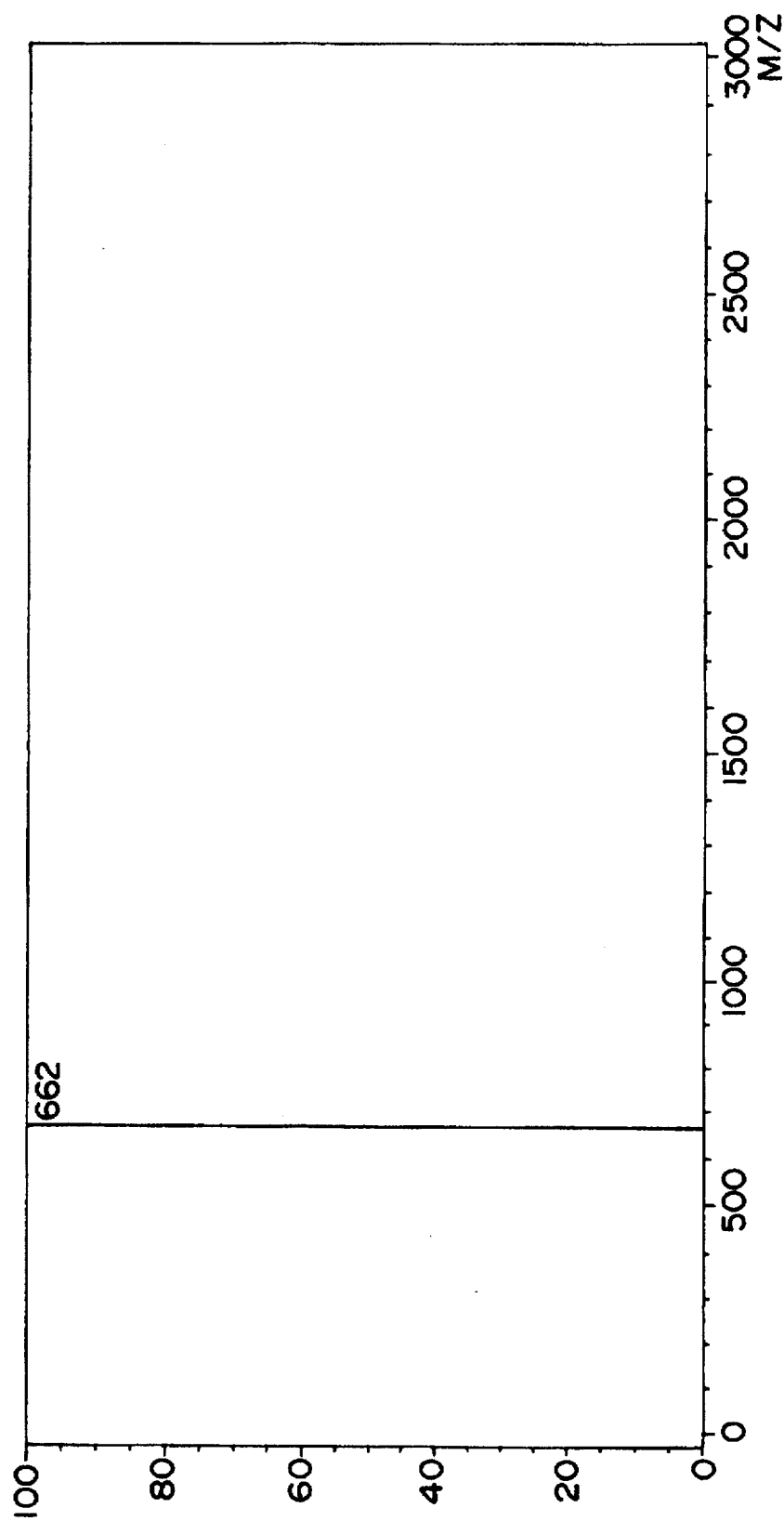
FIGS. 1, 2 and 3 are charts showing the results of electrolytic desorption ionization mass analysis, proton nuclear magnetic resonance spectroscopy and $^{13}C$ nuclear magnetic resonance spectroscopy of (hexadecylsalicylic acid) hexadecylphenyl ester obtained in Example 27, respectively.

An additive for a lubricant or a fuel of the present invention comprises at least one selected from the group consisting of substituted hydroxyaromatic ester derivatives represented by the general formulae (I) and (II)

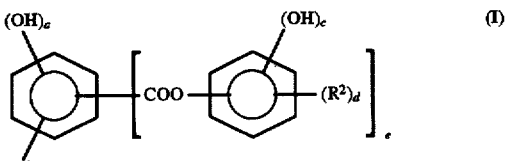

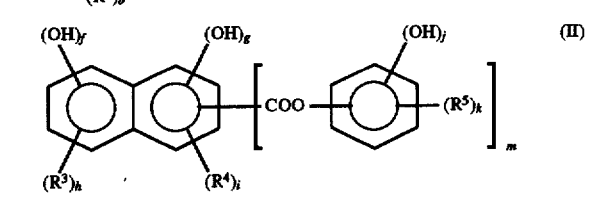

and this additive is useful as an ashless detergent in place of a metal detergent.

Furthermore, the additive for the lubricant of the present invention is also useful as an anti-wear agent, and the additive for the fuel of the present invention is also useful as the ashless detergent, as the anti-wear agent for preventing the abrasion of an injection pump which is triggered by the drop of a sulfur content in a gas oil, and as a storage stabilizer for a diesel gas oil composition to which a particulate reducer such as a polyoxyethylene compound is added.

In the above-mentioned general formulae (I) and (II), $R^1$, $R^2$, $R^3$, $R^4$ and $R^5$ are each an organic group having 6 or more carbon atoms. Examples of the organic group having 6 or more or more carbon atoms include hydrocarbon groups having preferably 6 to 7,000 carbon atoms, more preferably 8 to 225 carbon atoms. Examples of the hydrocarbon groups include an alkyl group, an alkenyl group, a cycloalkyl group, a cycloalkenyl group and an aralkyl group, and they may have a non-hydrocarbon substituent and a hetero-atom in a chain or a ring. Typical examples of the hydrocarbon groups include hydrocarbon groups such as a hexyl group, an octyl group, a nonyl group, a decyl group, a dodecyl group, a hexadecyl group and a triacontyl group, and groups derived from olefin polymers such as polyethylene, polypropylene and polybutene. In the case that the substituted hydroxyaromatic ester derivative having a low viscosity is desired, it is preferred that $R^1$, $R^2$, $R^3$, $R^4$ and $R^5$ are substantially straight-chain hydrocarbon groups. $R^1$ and $R^2$ may be the same or different, and $R^3$, $R^4$ and $R^5$ may be the same or different.

In the general formula (I), a, b, c, d and e are integers satisfying the relations of $1 \leq a \leq 3$, $1 \leq b \leq 3$, $0 \leq c \leq 3$, $1 \leq d \leq 3$, $1 \leq e \leq 3$, $3 \leq (a+b+e) \leq 6$ and $1 \leq (c+d) \leq 5$, respectively. In the case that b is 2 or 3, a plurality of $R^1$s may be the same or different, and in the case that d is 2 or 3, a plurality of R2s may be the same or different.

In the general formula (II), f, g, h, i, j, k and m are integers satisfying the relations of $0 \leq f \leq 3$, $0 \leq g \leq 3$, $1 \leq (f+g) \leq 3$, $0 \leq h \leq 4$, $0 \leq i \leq 3$, $1 \leq (h+i) \leq 6$, $0 \leq j \leq 3$, $1 \leq k \leq 3$, $1m \leq 3$, $3 \leq (f+g+h+i+m) \leq 8$ and $i \leq (j+K) \leq 5$, respectively. In the case that h is 2, 3 or 4, a plurality of $R^3$s may be the same or different, and in the case that i is 2 or 3, a plurality of R4s may be the same or different. Moreover, in the case that k is 2 or 3, a plurality of $R^5$s may be the same or different.

Typical examples of the substituted hydroxyaromatic ester derivatives represented by the general formula (I) include (hexylhydroxybenzoic acid) hexylphenyl ester, (hexylhydroxybenzoic acid) dodecylphenyl ester, (octylhydroxybenzoic acid) octylphenyl ester, (nonylhydroxybenzoic acid) nonylphenyl ester, (nonylhydroxybenzoic acid) hexadecylphenyl ester, (dodecylhydroxybenzoic acid) nonylphenyl ester, (dodecylhydroxybenzoic acid) dodecylphenyl ester, (dodecylhydroxybenzoic acid) hexadecylphenyl ester, (hexadecylhydroxybenzoic acid) hexylphenyl ester, (hexadecylhydroxybenzoic acid) dodecylphenyl ester, (hexadecylhydroxybenzoic acid) hexadecylphenyl ester, (eicosylhydroxybenzoic acid) eicosylphenyl ester, (mixed $C_{11}$–$C_{15}$ alkylhydroxybenzoic acid) mixed $C_{11}$–$C_{15}$ alkylphenyl esters, [long-chain alkyl (e.g., a group derived from a polydecene having 30 or more carbon atoms, or a group derived from a polybutene having a weight-average molecular weight of 400 or more) hydroxybenzoic acid] dodecylphenyl ester, [long-chain alkyl (e.g., a group derived from a polydecene having 30 or more carbon atoms, or a group derived from a polybutene having a weight-average molecular weight of 400 or more) hydroxybenzoic acid]long-chain alkyl (e.g., a group derived from a polydecene having 30 or more carbon atoms, or a group derived from a polybutene having a weight-average molecular weight of 400 or more) phenyl ester, (hexylhydroxybenzoic acid) hexylhydroxyphenyl ester, (octylhydroxybenzoic acid) octylhydroxyphenyl ester, (dodecylhydroxybenzoic acid) nonylhydroxyphenyl ester, (dodecylhydroxybenzoic acid) dodecylhydroxyphenyl ester, (hexadecylhydroxybenzoic acid) dodecylhydroxyphenyl ester, (hexadecylhydroxybenzoic acid) hexadecylhydroxyphenyl ester, (eicosylhydroxybenzoic acid) eicosylhydroxyphenyl ester, (mixed $C_{11}$–$C_{15}$ alkylhydroxybenzoic acid) mixed $C_{11}$–$C_{15}$ alkylhydroxyphenyl esters, [long-chain alkyl (e.g., a group derived from a polydecene having 30 or more carbon atoms, or a group derived from a polybutene having a weight-average molecular weight of 400 or more) hydroxybenzoic acid] dodecylhydroxyphenyl ester, [long-chain alkyl (e.g., a group derived from a polydecene having 30 or more carbon atoms, or a group derived from a polybutene having a weight-average molecular weight of 400 or more) hydroxybenzoic acid] long-chain alkyl (e.g., a group derived from a polydecene having 30 or more carbon atoms, or a group derived from a polybutene having a weight-average molecular weight of 400 or more) hydroxyphenyl ester, (hexyldihydroxybenzoic acid) hexylphenyl ester, (nonyldihydroxybenzoic acid) nonylphenyl ester, (nonyldihydroxybenzoic acid) dodecylphenyl ester, (dodecyldihydroxybenzoic acid) nonylphenyl ester, (dodecyldihydroxybenzoic acid) dodecylphenyl ester, (hexadecyldihydroxybenzoic acid) hexadecylphenyl ester, (eicosyldihydroxybenzoic acid) hexadecylphenyl ester, (eicosyldihydroxybenzoic acid) eicosylphenyl ester, (mixed $C_{11}$–$C_{15}$ alkyldihydroxybenzoic acid) mixed $C_{11}$–$C_{15}$ alkylphenyl esters, [long-chain alkyl (e.g., a group derived from a polydecene having 30 or more carbon atoms, or a group derived from a polybutene having a weight-average molecular weight of 400 or more) dihydroxybenzoic acid] dodecylphenyl ester, [long-chain alkyl (e.g., a group derived from a polydecene having 30 or more carbon atoms, or a group derived from a polybutene having a weight-average molecular weight of 400 or more) dihydroxybenzoic acid] long-chain alkyl (e.g., a group derived from a polydecene having 30 or more carbon atom, or a group derived from a polybutene having a weight-average molecular weight of 400 or more) phenyl ester, (hexyldihydroxybenzoic acid) hexylhydroxyphenyl ester, (nonyldihydroxybenzoic acid) nonylhydroxyphenyl ester, (nonyldihydroxybenzoic acid) dodecylhydroxyphenyl ester, (dodecyldihydroxybenzoic acid) nonylhydroxyphenyl ester, (dodecyldihydroxybenzoic acid) dodecylhydroxyphenyl ester, (hexadecyldihydroxybenzoic acid) hexadecylhydroxyphenyl ester, (eicosyldihydroxybenzoic acid) hexadecylhydroxyphenyl ester, (eicosyldihydroxybenzoic acid) eicosylhydroxyphenyl ester, (mixed $C_{11}$–$C_{15}$ alkyldihydroxybenzoic acid) mixed $C_{11}$–$C_{15}$ alkylhydroxyphenyl esters, [long-chain alkyl (e.g., a group derived from a polydecene having 30 or more carbon atoms, or a group derived from a polybutene having a weight-average molecular weight of 400 or more) dihydroxybenzoic acid] dodecylhydroxyphenyl ester, and [long-chain alkyl (e.g., a group derived from a polydecene having 30 or more carbon atoms, or a group derived from a polybutene having a weight-average molecular weight of 400 or more) dihydroxybenzoic acid] long-chain alkyl (e.g., a group derived from a polydecene having 30 or more carbon atoms, or a group derived from a polybutene having a weight-average molecular weight of 400 or more) hydroxyphenyl ester.

On the other hand, typical examples of the substituted hydroxyaromatic ester derivatives represented by the general formula (II) include (hexylhydroxynaphthoic acid) hexylphenyl ester, (hexylhydroxynaphthoic acid) hexadecylphenyl ester, (nonylhydroxynaphthoic acid) nonylphenyl ester, (dodecylhydroxynaphthoic acid) dodecylphenyl ester, (hexadecylhydroxynaphthoic acid) hexyldecylphenyl ester, (dodecylhydroxynaphthoic acid) eicosylphenyl ester, (eicosylhydroxynaphthoic acid) eicosylphenyl ester, (mixed $C_{11}$–$C_{15}$ alkylhydroxynaphthoic acid) mixed $C_{11}$–$C_{15}$ alkylphenyl esters, [long-chain alkyl (e.g., a group derived from a polydecene having 30 or more carbon atoms, or a group derived from a polybutene having a weight-average molecular weight of 400 or more) hydroxynaphthoic acid] dodecylphenyl ester, [long-chain alkyl (e.g., a group derived from a polydecene having 30 or more carbon atoms, or a group derived from a polybutene having a weight-average molecular weight of 400 or more) hydroxynaphthoic acid] long-chain alkyl (e.g., a group derived from a polydecene having 30 or more carbon atoms, or a group derived from a polybutene having a weight-average molecular weight of 400 or more) phenyl ester, (hexylhydroxynaphthoic acid) dodecylhydroxyphenyl ester, (octylhydroxynaphthoic acid) dodecylhydroxyphenyl ester, (dodecylhydroxynaphthoic acid) dodecylhydroxyphenyl ester, (dodecylhydroxynaphthoic acid) hexadecylhydroxyphenyl ester, (hexadecylhydroxynaphthoic acid) hexadecylhydroxyphenyl ester, (hexadecylhydroxynaphthoic acid) eicosylhydroxyphenyl ester, (mixed $C_{11}$–$C_{15}$ alkylhydroxynaphthoic acid) mixed $C_{11}$–$C_{15}$ alkylhydroxyphenyl esters, [long-chain alkyl (e.g., a group derived from a polydecene having 30 or more carbon atoms, or a group derived from a polybutene having a weight-average molecular weight of 400 or more) hydroxynaphthoic acid] dodecylhydroxyphenyl ester, [long-chain alkyl (e.g., a group derived from a polydecene having 30 or more carbon atoms, or a group derived from a polybutene having a weight-average molecular weight of 400 or more) hydroxynaphthoic acid] long-chain alkyl (e.g., a group derived from a polydecene having 30 or more carbon atoms, or a group derived from a polybutene having a weight-average molecular weight of 400 or more) hydroxyphenyl ester, (hexyldihydroxynaphthoic acid) hexylphenyl ester, (hexyldihydroxynaphthoic acid) hexadecylphenyl ester, (nonyldihydroxynaphthoic acid) nonylphenyl ester, (dodecyldihydroxynaphthoic acid) dodecylphenyl ester, (dodecyldihydroxynaphthoic acid) eicosylphenyl ester, (hexadecyldihydroxynaphthoic acid) hexadecylphenyl ester, (eicosyldihydroxynaphthoic acid) eicosylphenyl ester, (mixed $C_{11}$–$C_{15}$ alkyldihydroxynaphthoic acid) mixed $C_{11}$–$C_{15}$ alkylphenyl esters, [long-chain alkyl (e.g., a group derived from a polydecene having 30 or more carbon atoms, or a group derived from a polybutene having a weight-average molecular weight of 400 or more) dihydroxynaphthoic acid] dodecylphenyl ester, [long-chain alkyl (e.g., a group derived from a polydecene having 30 or more carbon atoms, or a group derived from a polybutene having a weight-average molecular weight of 400 or more) dihydroxynaphthoic acid] long-chain alkyl (e.g., a group derived from a polydecene having 30 or more carbon atoms, or a group derived from a polybutene having a weight-average molecular weight of 400 or more) phenyl ester, (hexyldihydroxynaphthoic acid) dodecylhydroxyphenyl ester, (octyldihydroxynaphthoic acid) dodecylhydroxyphenyl ester, (dodecyldihydroxynaphthoic acid) dodecylhydroxyphenyl ester, (dodecyldihydroxynaphthoic acid) hexadecylhydroxyphenyl ester, (hexadecyldihydroxynaphthoic acid) hexadecylhydroxyphenyl ester, (hexadecyldihydroxynaphthoic acid) eicosylhydroxyphenyl ester, (mixed $C_{11}$–$C_{15}$ alkyldihydroxynaphthoic acid) mixed $C_{11}$–$C_{15}$ alkylhydroxyphenyl esters, [long-chain alkyl (e.g., a group derived from a polydecene having 30 or more carbon atoms, or a group derived from a polybutene having a weight-average molecular weight of 400 or more) dihydroxynaphthoic acid] dodecylhydroxyphenyl ester, and [long-chain alkyl (e.g., a group derived from a polydecene having 30 or more carbon atoms, or a group derived from a polybutene having a weight-average molecular weight of 400 or more) dihydroxynaphthoic acid] long-chain alkyl (e.g., a group derived from a polydecene having 30 or more carbon atoms, or a group derived from a polybutene having a weight-average molecular weight of 400 or more) hydroxyphenyl ester.

Of these substituted hydroxyaromatic ester derivatives, preferable examples are compounds represented by the general formula (III)

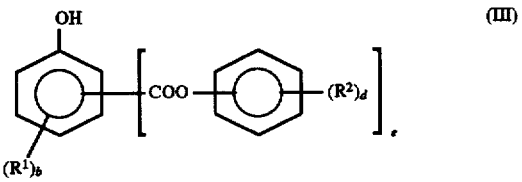

wherein $R^1$, $R^2$, b, d and e are as defined above, and the total of b and e is in the range of 2 to 5, and the general formula (III')

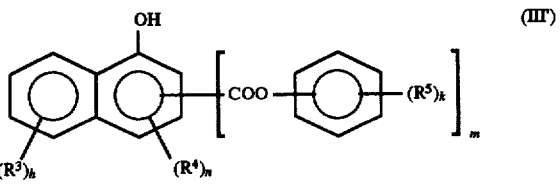

wherein $R^3$, $R^4$, $R^5$, h, k and m are as defined above, n is 0, 1 or 2, the total of h and n is in the range of 1 to 6, and the total of h, n and m is in the range of 2 to 7.

The additive for the lubricant or the additive for the fuel of the present invention may comprise one, two or more of the compounds represented by the above-mentioned general formula (I). Alternatively, it may comprise one, two or more of the compounds represented by the above-mentioned general formula (II). Moreover, it may comprise one or more of the compounds represented by the above-mentioned general formula (I) and one or more of the compounds represented by the above-mentioned general formula (II).

No particular restriction is put on a preparation process of the substituted hydroxyaromatic ester derivative represented by the general formula (I), but, for example, this substituted hydroxyaromatic ester derivative represented by the general formula (I) can be obtained by reacting at least one of organic group-substituted hydroxybenzenecarboxylic acids represented by the general formula

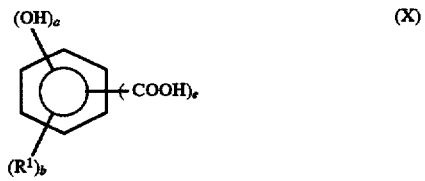

wherein $R^1$, a, b and e are as defined above, with at least one of organic group-substituted phenols represented by the general formula (XI)

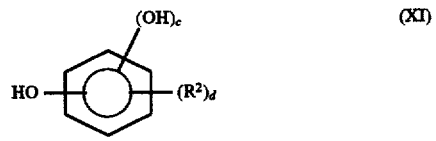

wherein $R^2$, c and d are as defined above.

On the other hand, with regard to a preparation process of the substituted hydroxyaromatic ester derivative represented by the general formula (II), no particular restriction is put on it, but for example, this derivative of the general formula (II) can be obtained by reacting at least one of organic group-substituted hydroxynaphthalenecarboxylic acids represented by the general formula (XII)

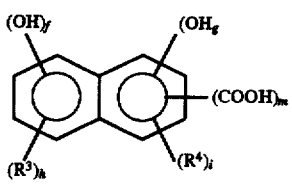

wherein $R^3$, $R^4$, f, g, h, i and m are as defined above, with at least one of organic group-substituted phenols represented by the general formula (XIII)

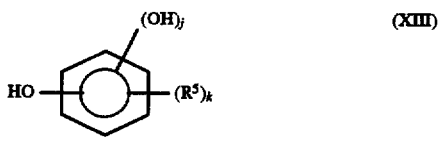

wherein $R^5$, j and k are as defined above.

In these reactions, a molar ratio of the organic group-substituted hydroxyaromaticcarboxylic acid to the organic group-substituted phenol is in the range of 1:0.01 to 1:4, preferably 1:0.2 to 1:2.5. Furthermore, a reaction temperature is selected within the range of usually 100 to 300° C., preferably 150 to 250° C. This reaction may be carried out in the absence of any catalyst or in the presence of an acid catalyst or an alkaline catalyst. In carrying out this reaction, a solvent such as a hydrocarbon oil can be used.

The above-mentioned organic group-substituted hydroxyaromaticcarboxylic acid can be prepared by any of various methods, and one example thereof comprises reacting an alkali metal salt of an organic group-substituted phenol or naphthol with carbon dioxide in accordance with a known Kolbe-Schmitt reaction, and then hydrolyzing the resultant reaction product.

Next, an additive composition for a lubricant or a fuel of the present invention comprises, as a component (a), the additive for the lubricant or the fuel comprising at least one selected from the group consisting of substituted hydroxyaromatic ester derivatives represented by the above-mentioned general formulae (I) and (II), and, as a component (b), an ashless detergent. This kind of additive composition can be used as an ashless detergent dispersant which is excellent in high-temperature stability (high-temperature detergency) and which has a particles dispersion function.

No particular restriction is put on the kind of ashless dispersant which is the component (b), and there can be used conventional known dispersants. For example, carboxylic acid imides, carboxylic acid esters and hydroxybenzylamines can be used singly or in a combination. The preferable acidic moiety of each of the carboxylic acid imides and carboxylic acid esters is preferably succinic acid, and each of the carboxylic acid imides and carboxylic acid esters preferably has a hydrocarbon group having a molecular weight of 200 or more in the molecular structure. This hydrocarbon group is an alkyl group or an alkenyl group, and it may have a non-hydrocarbon substituent and a heteroatom in a chain or a ring.

The carboxylic acid imide and the carboxylic acid ester are a reaction product of a carboxylic acid derivative with (1) an organic nitrogen compound having at least one —NH— group such as an amine, urea or hydrazine and a reaction product of the carboxylic acid derivative with (2) a hydroxy compound such as a phenol or an alcohol, respectively. Each of the carboxylic acid imide and the carboxylic acid ester may contain a reaction product of the carboxylic acid derivative with a reactive metal or a reactive metallic compound, so far as its amount has no influence on the effect. In addition, products obtained by subjecting these reaction products to a post-treatment are also useful as the component (b). Examples of a post-treatment agent include sulfur, sulfur compounds, urea, thiourea, guanidine, aldehydes, ketones, carboxylic acids, hydrocarbon-substituted succinic anhydrides, nitriles, epoxides, boron compounds and phosphorus compounds (the details of these carboxylic acid imides and carboxylic acid esters are described in Japanese Patent Publication No. 60876/1991).

On the other hand, the above-mentioned hydroxybenzylamine is, for example, a reaction product of a hydrocarbon-substituted phenol such as a sulfur-crosslinked phenol or a methylene-crosslinked phenol, formaldehyde and a nitrogen compound having at least two —NH— groups, for example a polyamine.

In the additive composition for the lubricant or the fuel of the present invention, a weight ratio of the component (a), i.e., the additive for the lubricant or the fuel which comprises at least one selected from the groups consisting of the substituted hydroxyaromatic ester derivatives represented by the general formulae (I) and (II) to the component (b), i.e., the ashless dispersant is in the range of 10:90 to 99:1, preferably 15:85 to 75:25.

A lubricating oil composition of the present invention can be prepared by adding, to a base oil for a lubricating oil, (a) at least one selected the group consisting of the substituted hydroxyaromatic ester derivatives represented by the above-mentioned general formulae (I) and (II) and, optionally (b) the ashless dispersant. The components (a) and (b) are each suitably blended with the base oil in amounts of 1 to 30 wt %, preferably 2 to 20 wt % based on the total weight of the lubricating oil composition.

As the above-mentioned base oil for the lubricating oil, there can be used a mineral oil, a synthesized oil or a combination thereof. Examples of the mineral oil include fractions of paraffinic mineral oils, naphthenic mineral oils and aromatic mineral oils, and they may be used after treating by any refining method such as solvent refining, hydrofinishing, hydrocracking, and so on. Examples of the usable synthesized oil include polyphenyl ethers, polyvinyl ethers and hydrogenated/purified products thereof, alkylbenzenes, alkylnaphthalenes, esters, polyglycols and polyolefins. The fraction for the lubricating oil has a kinematic viscosity (100° C.) usually in the range of 1 to 50 cSt, preferably in the range of 3 to 10 cSt.

As the synthesized oil comprising the ester, there can be used a synthesized oil comprising an ester of a monobasic acid or a dibasic acid and an alcohol, for example, an ester obtained by reacting a dibasic acid having 6 to 16 carbon atoms with a straight-chain or a branched alcohol having 5 to 20 carbon atom. Examples of the particularly preferable esters include adipates, sebacates, azelates, trimethylolpropane esters, trimethylolethane esters, pentaerythritol esters and neopentyl glycol esters. As the synthesized oil comprising the polyolefin, suitable are liquid products obtained by low polymerization or copolymerization of lower olefins such as ethylene, propylene, butylene, octene, decene and dodecene, mixtures of these liquid products, and hydrogenated/purified products thereof. In addition, composite esters comprising dibasic acids, glycol, monobasic acids and the like as well as α-olefin-dibasic acid copolymer esters are also usable.

In the lubricating oil composition of the present invention, as the base oil, the above-mentioned mineral oils may be used singly or in a combination of two or more thereof, or the above-mentioned synthesized oils may be used singly or in a combination of two or more thereof, or one or more of the mineral oils and one or more of the synthesized oils may be used in combination.

The lubricating oil composition of the present invention, if necessary, can be blended with various kinds of additive components which have usually been used in a conventional lubricating oil composition, for example, an antioxidant, an anticorrosive agent, an anti-foaming agent, a viscosity index improver, a pour point depressant, an anti-wear agent, a demulsifier and a metal detergent, in addition to the above-mentioned additive composition for the lubricant, so far as the objects of the present invention are not impaired.

A fuel composition of the present invention can be prepared by adding, to a fuel, (a) at least one selected from the substituted hydroxyaromatic ester derivatives represented by the above-mentioned general formulae (I) and (II) and, as needed, (b) the above-mentioned ashless dispersant. The components (a) and (b) are each suitably blended with the fuel in an amount of 0.005 to 5.0 wt %, preferably 0.02 to 2 wt % based on the total weight of the fuel composition. Examples of the fuel include gasoline, kerosine and gas oil.

The fuel composition of the present invention has excellent detergent functions, and for example, it can prevent a deposit from adhering to the carburetor or the injector of an internal combustion engine, and it can also remove adhered materials.

The fuel composition of the present invention can be blended with suitable amounts of known additives for the fuel, for example, a detergent, a cetane number improver, an antioxidant, a metal inactivating agent, a fluidity improver, an anticorrosive agent, an organic metal complex fuel additive, a demulsifier and an oxygen-containing fuel additive, in addition to the above-mentioned additive composition for the fuel, so far as the objects of the present invention are not impaired.

The present invention also intends to provide novel substituted hydroxyaromatic ester derivatives, that is to say, a substituted hydroxyaromatic ester derivative represented by the general formula (IV)

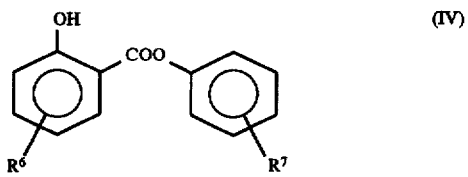

(IV)

wherein $R^6$ and $R^7$ are each an alkyl group having 9 to 20 carbon atoms, and they may be the same or different, and a substituted hydroxyaromatic ester derivative represented by the general formula (VII)

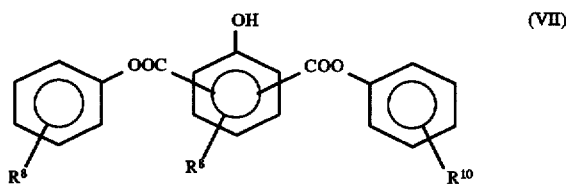

(VII)

wherein $R^8$, $R^9$ and $R^{10}$ are each a hydrocarbon group, and they may be the same or different.

In the general formula (IV), $R^6$ and $R^7$ are each an alkyl group having 9 to 20 carbon atoms, and examples of the alkyl group having 9 to 20 carbon atoms include hydrocarbon groups such as a nonyl group, a decyl group, a dodecyl group, a hexadecyl group, an octadecyl group and an eicosyl group, and groups derived from olefin polymers (e.g., polyethylene, polypropylene and polybutene).

When the low-viscosity substituted hydroxyaromatic ester derivative is desired, $R^6$ and $R^7$ preferably are each a substantially straight-chain hydrocarbon group.

In the general formula (VII), $R^8$, $R^9$ and $R^{10}$ are each a hydrocarbon group, and they may be the same or different. Furthermore, this substituted hydroxyaromatic ester derivative also includes a mixture of two or more kinds of substituted hydroxyaromatic ester derivatives represented by the general formula (VII).

Here, no particular restriction is put on the kind of hydrocarbon group, and examples of the hydrocarbon group include chain hydrocarbon groups (e.g., alkyl groups, alkenyl groups and alkinyl groups) and cyclic hydrocarbon groups (e.g., alicyclic hydrocarbon groups such as cycloparaffin groups and cycloolefin groups, and aromatic hydrocarbon groups such as a phenyl group and a naphthyl group). Above all, chain hydrocarbon groups such as the alkyl groups and the alkenyl groups are preferable. These hydrocarbon groups may be substituted by another hydrocarbon group such as a lower alkyl group, a cycloalkyl group or a phenyl group. In addition, the hydrocarbon groups also include groups substituted by non-hydrocarbon groups, so far as they substantially maintain the characteristics of the hydrocarbon groups. Examples of the non-hydrocarbon groups by which the hydrocarbon groups may be substituted include a nitro group, an amino group, halogen atoms (e.g., chlorine and bromine), nitrohydrocarbon groups, aminohydrocarbon groups, halogenated hydrocarbon groups, lower alkoxy groups, lower alkylthio groups, an oxo group (=O), a thiooxo group (=S) and interruption groups (e.g., —NH—, —O— and —S—).

Typical examples of the hydrocarbon groups include a propyl group, a butyl group, an isobutyl group, a pentyl group, a hexyl group, a 1-methylhexyl group, a 2,3,5-trimethylheptyl group, an octyl group, a 3-ethyloctyl group, a 4-ethyl-5-methyloctyl group, a nonyl group, a decyl group, a dodecyl group, a 2-methyl-4-ethyldodecyl group, a hexadecyl group, an octadecyl group, an eicosyl group, a docosyl group, a tetracontyl group, a 4-hexenyl group, a 2-ethyl-4-hexenyl group, a 6-octenyl group, a 3-cyclohexyloctyl group, a phenylnonyl group, a nitrododecyl group, a 3-aminononyl group, a chlorohexadecyl group, a (2-nitroethyl)octyl group, a (3-aminocyclohexyl)nonyl group, a 4-(p-chlorophenyl)octyl group, a 4-butoxyhexadecyl group, a 3-propylthiooctadecyl group, a 5-propanoylnonyl group, an ethanethioylhexadecyl group, and hydrocarbon groups derived from olefin polymers (e.g., polyethyelne, polypropylene, polybutene, ethylene-propylene copolymer, polychloroprene, chlorinated olefin polymers and oxidized ethylene-propylene copolymer).

Of the above-mentioned hydrocarbon groups, straight-chain and branched alkyl groups are preferable. Above all, the alkyl groups having 4 to 20 carbon atoms are preferable, and the alkyl groups having 9 to 16 carbon atoms are more preferable. In particular, it is preferred that the carbon number of $R^8$ is limited as mentioned above.

Typical examples of the preferable alkyl groups include straight-chain and branched alkyl groups such as a butyl group, an isobutyl group, a pentyl group, a hexyl group, a 1-methylhexyl group, a heptyl group, a 2,3,5-trimethylheptyl group, an octyl group, a 3-ethyloctyl group, a 4-ethyl-5-methyloctyl group, a nonyl group, a decyl group, a dodecyl group, a 2-methyl-4-ethyldodecyl group, a hexadecyl group, an octadecyl group and an eicosyl group, and straight-chain and branched alkyl groups derived from olefin polymers (e.g., polyethyelne, polypropylene, polybutene and ethylene-propylene copolymer).

When the low-viscosity substituted hydroxyaromatic ester derivative is desired, $R^8$, $R^9$ and $R^{10}$ preferably are each a substantially straight-chain hydrocarbon group.

The substituted hydroxyaromatic ester derivatives represented by the general formulae (IV) and (VII) are novel compounds, and these derivatives are useful as ashless dispersants excellent in high-temperature stability (high-temperature detergency) which can be substituted for the metal detergents. Therefore, they can be suitably used as additives for the lubricant for engine oils, above all, a diesel engine oil and a methanol engine oil which can comply with future severe exhaust gas controls, and as additives for the fuel for an internal combustion engine.

Furthermore, the substituted hydroxyaromatic ester derivatives can be used as anti-wear agents for preventing the abrasion of an injection pump which is caused by the drop of a sulfur content in a gas oil, and as storage stabilizers for a diesel gas oil composition to which a particulate reducer such as a polyoxyethylene compound is added.

According to a method of the present invention, the substituted hydroxyaromatic ester derivative represented by the above-mentioned general formula (IV) of the present invention can be prepared by reacting an alkyl group-substituted salicylic acid represented by the general formula (V)

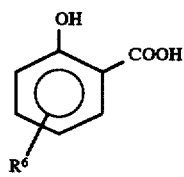

wherein $R^6$ is as defined above, with an alkyl-substituted phenol represented by the general formula (VI)

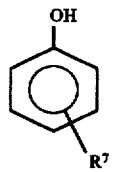

wherein $R^7$ is as defined above, in the presence of no catalyst or a catalyst.

In this reaction, a molar ratio of the alkyl group-substituted salicylic acid to the alkyl-substituted phenol is suitably in the range of 1:0.01 to 1:3, preferably 1:0.2 to 1:1.5. A reaction temperature can be selected usually in the range of 100° to 300° C., preferably 150° to 250° C. This reaction may be carried out in the absence of any catalyst or in the presence of an acid catalyst or an alkaline catalyst. In carrying out this reaction, a solvent such as a hydrocarbon oil can be used.

The above-mentioned alkyl group-substituted salicylic acid can be prepared, for example, by reacting an alkali metal salt of an alkyl group-substituted phenol with carbon dioxide in accordance with a known Kolbe-Schmitt reaction, and then hydrolyzing the resultant reaction product.

Examples of this alkyl group-substituted salicylic acid include nonylsalicylic acid, decylsalicylic acid, dodecylsalicylic acid, hexadecylsalicylic acid, octadecylsalicylic acid and eicosylsalicylic acid.

Examples of the alkyl group-substituted phenol include nonylphenol, decylphenol, dodecylphenol, hexadecylphenyl, octadecylphenol and eicosylphenol.

No particular restriction is put on the position of each alkyl group in the alkyl group-substituted salicylic acid and the alkyl group-substituted phenol.

On the other hand, according to a method of the present invention, the substituted hydroxyaromatic ester derivative represented by the above-mentioned general formula (VII) of the present invention can be prepared by reacting a hydrocarbon group-substituted hydroxybenzenedicarboxylic acid represented by the general formula (VIII)

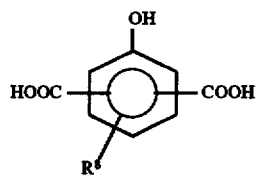

wherein $R^8$ is as defined above, with at least one of hydrocarbon group-substituted phenols represented by the general formula (IX)

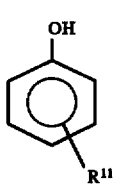

wherein $R^{11}$ is $R^9$ or $R^{10}$, and it is a hydrocarbon group, in the presence of no catalyst or a catalyst.

In this reaction, when only one kind of hydrocarbon group-substituted phenol is used, the substituted hydroxyaromatic ester derivative having the general formula (VII) in which $R^9$ and $R^{10}$ are the same can be obtained. On the other hand, when two or more kinds of hydrocarbon group-substituted phenols are used, the substituted hydroxyaromatic ester derivative having the general formula (VII) in which $R^9$ and $R^{10}$ are different can be obtained. In this connection, two or more kinds of hydrocarbon group-substituted phenols may simultaneously be reacted with the hydrocarbon group-substituted hydroxybenzenedicarboxylic acid, or they may be separately reacted therewith by changing the timing of the reaction, an apparatus to be used, or the like.

No particular restriction is put on a molar ratio of the hydrocarbon group-substituted hydroxybenzenedicarboxylic acid to the hydrocarbon group-substituted phenol, but this molar ratio is suitably in the range of 1:0.01 to 1:4, preferably 1:0.4 to 1:2.5. In the case that two or more kinds of hydrocarbon group-substituted phenols are used, the total amount of all the hydrocarbon group-substituted phenols is preferably within the above-mentioned range.

No particular restriction is put on a reaction temperature, either, but it is usually selected in the range of 100° to 300° C., preferably 150° to 250° C. This reaction may be carried out in the absence of any catalyst or in the presence of an acid catalyst or an alkaline catalyst. Examples of the acid catalyst include mineral acids and organic acids, and examples of the alkaline catalyst include alkali metals and alkaline earth metals. In carrying out this reaction, a solvent such as a hydrocarbon oil can be used.

Typical examples of the hydrocarbon group-substituted hydroxybenzenedicarboxylic acid represented by the general formula (VIII) include butyl hydroxybenzenedicarboxylic acid, hexyl hydroxybenzenedicarboxylic acid, octyl hydroxybenzenedicarboxylic acid, nonyl hydroxybenzenedicarboxylic acid, decyl hydroxybenzenedicarboxylic acid, dodecyl hydroxybenzenedicarboxylic acid, hexadecyl hydroxybenzenedicarboxylic acid, octadecyl hydroxybenzenedicarboxylic acid and eicosyl hydroxybenzenedicarboxylic acid.

The hydrocarbon group-substituted hydroxybenzenedicarboxylic acid represented by the general formula (VIII)

can be prepared, for example, by reacting an alkali metal salt of a hydrocarbon group-substituted phenol with carbon dioxide in accordance with a known Kolbe-Schmitt reaction, and then hydrolyzing the resultant reaction product.

Typical examples of the hydrocarbon group-substituted phenol represented by the general formula (IX) include butylphenol, hexylphenol, octylphenol, nonylphenol, decylphenol, dodecylphenol, hexadecylphenyl, octadecylphenol and eicosylphenol.

No particular restriction is put on the position of each hydrocarbon group in the hydrocarbon group-substituted hydroxybenzenedicarboxylic acid represented by the general formula (VIII) and the hydrocarbon group-substituted phenol represented by the general formula (IX).

The substituted hydroxyaromatic ester derivatives of the present invention represented by the general formulae (IV) and (VII) are useful as ashless dispersants, as described above. For example, when the substituted hydroxyaromatic ester derivative as the component (a) is combined with the ashless dispersant as the component (b), an additive composition for a lubricant or a fuel can be prepared which is desirable as an ashless detergent dispersant excellent in high-temperature stability (high-temperature detergency) and having a particles dispersion function.

Next, the present invention will be described in detail with reference to examples, but the scope of the present invention should not be limited to these examples at all.

REFERENCE EXAMPLE 1

In a 2-liter autoclave were placed 1,100 g of polybutene (Mw=987), 6.4 g (0.021 mol) of cetyl bromide and 115 g (1.2 mol) of maleic anhydride. Afterward, the autoclave was purged with nitrogen, and reaction was then carried out at 240° C. for 5 hours. The reaction system was heated up to 215° C., and unreacted maleic anhydride and cetyl bromide were then distilled off under reduced pressure. Next, the temperature of the reaction system was lowered to 140° C, followed by filtration. The yield of the resultant polybutenylsuccinic anhydride was 1,099 g.

In a 2-liter separable flask were placed 500 g of the thus obtained polybutenylsuccinic anhydride, 64 g (0.34 mol) of tetraethylenepentamine (TEPA, made by Toso Co., Ltd.) and 300 g of a mineral oil, and reaction was then carried out at 150° C. for 2 hours under nitrogen gas stream. Afterward, the reaction system was heated up to 200° C., and the unreacted TEPA and produced water were then distilled off under reduced pressure. Next, the temperature of the reaction system was lowered to 140° C., followed by filtration. The yield of the resultant polybutenylsuccinimide was 784 g.

In a 500-milliliter separable flask were placed 240 g of the obtained polybutenylsuccinimide and 28 g of boric acid, and reaction was then carried out at 150° C. for 4 hours under nitrogen gas stream. Afterward, produced water were distilled off at 150° C. under reduced pressure, and the temperature of the reaction system was lowered to 140° C., followed by filtration. The yield of the resultant reaction product was 231 g.

EXAMPLE 1

In a 1-liter flask were placed 319 g (1 mol) of hexadecylphenyl (a reaction product of 1-hexadecene and phenol) and 200 g of xylene, and they were then stirred so as to become a uniform mixture. Afterward, the mixture was heated up to 70° C., and 80 g of a 48 wt % aqueous NaOH solution was added thereto. Under nitrogen gas stream, xylene was refluxed for 2 hours to distill off water. The reaction solution was transferred to a 1-liter autoclave, and it was then pressurized to 10 kg/cm$^2$G by carbon dioxide and reaction was carried out at 155° C. for 1 hour. Next, the temperature of the reaction system was lowered to 80° C., and the solution was then transferred to a 2-liter flask. To this flask, 120 g of xylene was added, followed by stirring to uniform the solution. Afterward, 250 g of 20 wt % sulfuric acid was added thereto over 30 minutes, and reaction was then done for 1 hour. The resultant reaction solution was washed with water, and after phase separation and filtration, xylene was distilled off. The yield of the resultant reaction product was 312 g.

In a 500-milliliter flask were placed 300 g of the obtained reaction product and 100 g of hexadecylphenyl, and reaction was then carried out at 250° C. for 5 hours under nitrogen gas stream. Afterward, produced water and hexadecylphenyl were distilled off at 250° C. under reduced pressure. The yield of the resultant reaction product was 195 g.

According to the results of electrolytic desorption ionization mass analysis, proton nuclear magnetic resonance spectroscopy and $^{13}$C nuclear magnetic resonance spectroscopy, it was confirmed that this product was a mixture of compounds represented by the following formulae (XIV) and (XV). It was also confirmed from the results of liquid chromatograph analysis (a detector=a differential refractometer) that a ratio between the compounds represented by the formulae (XIV) and (XV) is the compound of the formula (XIV):the compound of the formula (XV)=78 area %:22 area %.

Formula (XIV): (hexadecylsalicylic acid) hexadecylphenyl ester

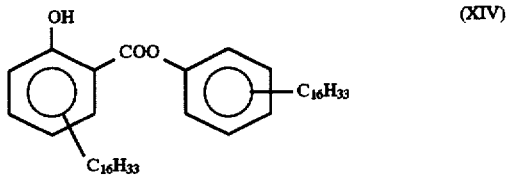

Formula (XV): (hexadecylhydroxybenzenedicarboxylic acid) bis(hexadecylphenyl) ester

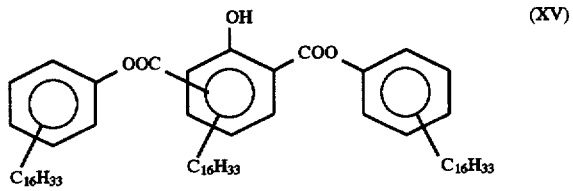

EXAMPLE 2

The same procedure as in Example 1 was carried out except that hexadecylphenyl was replaced with dodecylphenol (a reaction product of 1-dodecene and phenol).

This product was a mixture of compounds represented by the following formulae (XVI) and (XVII):

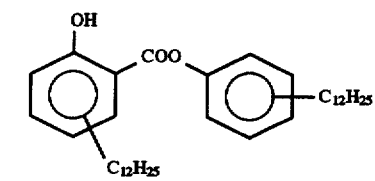

(XVI)

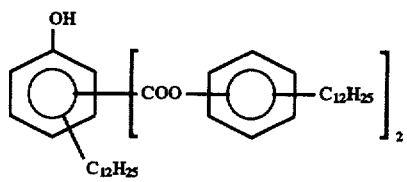

(XVII)

EXAMPLE 3

The same procedure as in Example 1 was carried out except that hexadecylphenyl was replaced with a mixture of dodecylphenol and dinonylphenol (a reaction product of propylene oligomer and phenol).

The resultant product was a mixture of compounds represented by the following formulae (XVIII) and (XIX):

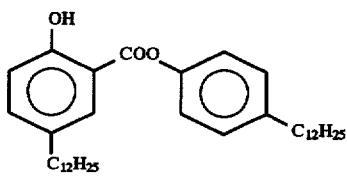

(XVIII)

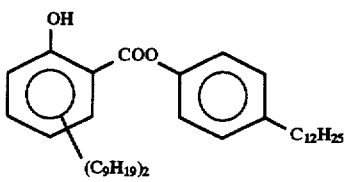

(XIX)

EXAMPLE 4

The same procedure as in Example 1 was carried out except that hexadecylphenyl was replaced with nonylphenol (a reaction product of propylene oligomer and phenol).

The resultant product was a mixture of compounds represented by the following formulae (XX) and (XXI):

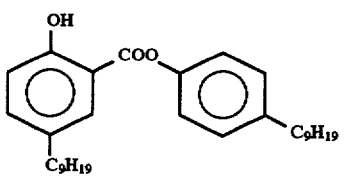

(XX)

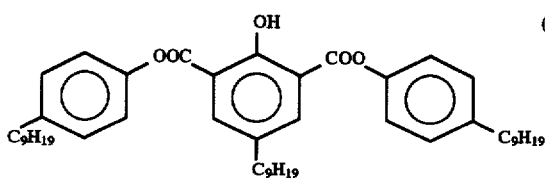

(XXI)

EXAMPLE 5

The same procedure as in Example 1 was carried out except that 5-octylsalicylic acid and p-octylphenol were used.

The resultant product was a compound represented by the following formula (XXII):

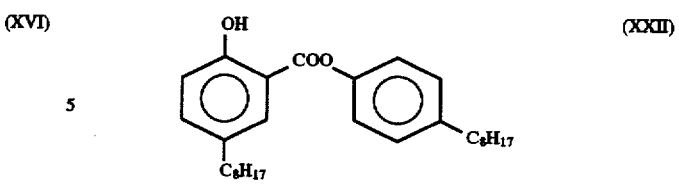

(XXII)

EXAMPLES 6 to 10

Preparation of additive compositions for lubricants (ashless detergent dispersants)

75 wt % of an ashless dispersant (boric acid-treated polybutenylsuccinimide) obtained in Reference Example 1 was blended with 25 wt % of each of substituted hydroxyaromatic ester derivatives obtained in Examples 1 to 5 to prepare additive compositions for lubricants.

EXAMPLES 11 to 15

Preparation of lubricating oil compositions

Each of additive compositions for lubricants obtained in Examples 6 to 10 was blended with a mineral oil which was a 500 neutral fraction to prepare lubricating oil compositions, and in this case, the amount of the additive composition was 10 wt % (2.5 wt % of a substituted hydroxyaromatic ester derivative and 7.5 wt % of an ashless dispersant) based on the total weight of each lubricating oil composition.

The performance of these lubricating oil compositions was evaluated in accordance with a hot tube test which would be described hereinafter. The results are shown in Table 1.

[Conditions of hot tube test]

A sample oil and air were caused to continuously flow at 0.3 ml/hr and 10 ml/min, respectively, through a glass tube having an inner diameter of 2 mm for 16 hours, while the temperature of the glass tube was maintained at 310° C. Next, a lacquer deposited onto the glass tube was compared to a color specimen, and it was graded on the basis of standards of transparency=10 points and black=0 point. Moreover, the weight of the lacquer deposited onto the glass tube was measured. The higher the grade is and the smaller the weight of the lacquer is, the more excellent the performance of the sample oil is.

COMPARATIVE EXAMPLE 1

The same procedure as in Example 1 was carried out except that hexadecylphenyl was replaced with dodecylphenol (a reaction product of propylene oligomer and phenol), followed by purification, thereby obtaining 5-dodecylsalicylic acid. Afterward, this 5-dodecylsalicylic acid was reacted with p-cresol in the same manner as in Example 1.

The resultant product was a compound represented by the following formula (XXIII):

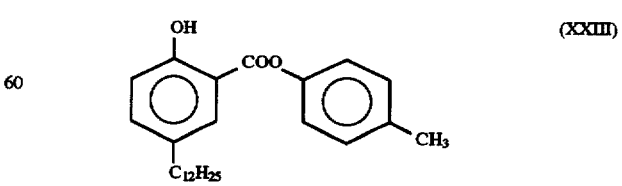

(XXIII)

Next, 2.5 wt % of the above-mentioned substituted hydroxyaromatic ester derivative and 7.5 wt % of an ashless dispersant of Reference Example 1 based on the total weight of a lubricating oil composition were blended with a mineral oil which was a 500 neutral fraction to prepare a lubricating oil composition. Its performance was evaluated by a hot tube test. The results are shown in Table 1.

COMPARATIVE EXAMPLE 2

The same procedure as in Comparative Example 1 was carried out except that 5-dodecylsalicylic acid was replaced with salicylic acid and p-cresol was replaced with hexadecylphenyl (a reaction product of 1-hexadecene and phenol).

The resultant product was a compound represented by the following formula (XXIV):

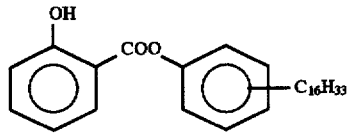

Next, the above-mentioned compound was used and the same procedure as in Comparative Example 1 was carried out to prepare a lubricating oil composition, and its performance was evaluated by a hot tube test. The results are shown in Table 1.

COMPARATIVE EXAMPLE 3

The same procedure as in Comparative Example 1 was carried out except that 5-dodecylsalicylic acid was replaced with 5-t-butylsalicylic acid and p-cresol was replaced with p-t-butylphenol.

The resultant product was a compound represented by the following formula (XXV):

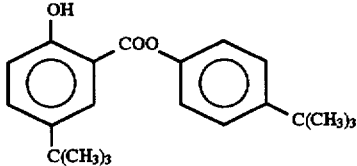

Next, the above-mentioned compound was used and the same procedure as in Comparative Example 1 was carried out to prepare a lubricating oil composition, and its performance was evaluated by a hot tube test. The results are shown in Table 1.

COMPARATIVE EXAMPLE 4

A compound represented by the following formula (XXVI) was used and the same procedure as in Comparative Example 1 was carried out to prepare a lubricating oil composition, and its performance was evaluated by a hot tube test. The results are shown in Table 1:

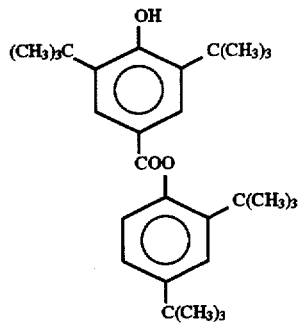

COMPARATIVE EXAMPLE 5

A compound represented by the following formula (XXVII) was used and the same procedure as in Comparative Example 1 was carried out to prepare a lubricating oil composition, and its performance was evaluated by a hot tube test. The results are shown in Table 1:

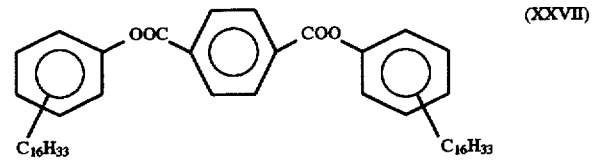

COMPARATIVE EXAMPLE 6

A compound represented by the following formula (XXVIII) was used and the same procedure as in Comparative Example 1 was carried out to prepare a lubricating oil composition, and its performance was evaluated by a hot tube test. The results are shown in Table 1:

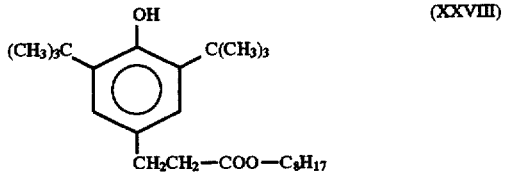

COMPARATIVE EXAMPLES 7 and 8

The same procedure as in Comparative Example 1 was carried out except that a substituted hydroxyaromatic ester derivative represented by the formula (XXIII) was replaced with overbased calcium phenate and overbased calcium salicylate which were metal detergents, respectively, to prepare lubricating oil compositions, and their performance was evaluated by a hot tube test. The results are shown in Table 1.

TABLE 1

| | Contained Detergent | | | Hot Tube Test (310° C.) | |
|---|---|---|---|---|---|
| | | Substituent | | | Deposit |
| | Kind | $R^1$ | $R^2$ | Grade | (mg) |
| Example 11 | Ester of Ex. 1 | $C_{16}H_{33}$ | $C_{16}H_{33}$ | 8 | 1> |
| Example 12 | Ester of Ex. 2 | $C_{12}H_{25}$ | $C_{12}H_{25}$ | 8 | 1> |
| Example 13 | Ester of Ex. 3 | $C_9H_{19}$ $C_{12}H_{25}$ | $C_{12}H_{25}$ | 8 | 1> |

TABLE 1-continued

| | | Contained Detergent | | Hot Tube Test (310° C.) | |
|---|---|---|---|---|---|
| | | Substituent | | | Deposit |
| | Kind | $R^1$ | $R^2$ | Grade | (mg) |
| Example 14 | Ester of Ex. 4 | $C_9H_{19}$ | $C_9H_{19}$ | 7 | 1> |
| Example 15 | Ester of Ex. 5 | $C_8H_{17}$ | $C_8H_{17}$ | 4 | 3 |
| Comp. Ex. 1 | Ester of Ex. 1 | $C_{12}H_{25}$ | CH3 | 0 | 12 |
| Comp. Ex. 2 | Ester of Ex. 2 | — | $C_{16}H_{33}$ | 2 | 7 |
| Comp. Ex. 3 | Ester of Ex. 3 | $C_4H_9$ | $C_4H_9$ | 0 | 13 |
| Comp. Ex. 4 | Ester of Ex. 4 | $C_4H_9$ | $C_4H_9$ | 0 | 11 |
| Comp. Ex. 5 | Ester of Ex. 5 | — | — | 0 | 45 |
| Comp. Ex. 6 | Ester of Ex. 6 | — | — | 0 | 13 |
| Comp. Ex. 7 | Perbasic Ca phenate | — | — | 0 | 78 |
| Comp. Ex. 8 | Perbasic Ca salicylate | — | — | 0 | 30 |

As understood from Table 1, the lubricating oil compositions regarding Examples 11 to 15, in which the additives for lubricants of the present invention were used, showed better results in the hot tube tests and more excellent high-temperature stability (high-temperature detergency), as compared with the lubricating oil compositions using the substituted and unsubstituted hydroxyaromatic ester derivatives in Comparative Examples 1 to 4, the aromatic ester derivative having no hydroxyl group in Comparative Example 5, octadecyl-3-(3,5-di-t-butyl-4-hydroxyphenyl) propionate in Comparative Example 6, and overbased calcium phenate and overbased calcium salicylate which were metal detergents in Comparative Examples 7 and 8.

EXAMPLES 16 and 17

Preparation of lubricating oil compositions

Each of substituted hydroxyaromatic ester derivatives obtained in Examples 1 and 2 was blended with a mineral oil which was a 150 neutral fraction, to prepare lubricating oil compositions, and in this case, the amount of each substituted hydroxyaromatic ester derivative was 5 wt % based on the total weight of the lubricating oil composition.

The performance of each lubricating oil composition was evaluated by the following shell four-ball test. The results are shown in Table 2.

[Shell four-ball test]

A shell wear depth (mm) was measured under a load of 30 kg at an oil temperature of 75° C. for 60 minutes in accordance with ASTM D-2783.

COMPARATIVE EXAMPLE 9

A mineral oil which was a 150 neutral fraction was evaluated by a shell four-ball test. The results are shown in Table 2.

TABLE 2

| | Contained Ester Derivative | | Shell Wear Depth (30 kg, 60 min, 75° C.) (mm) |
|---|---|---|---|
| | Kind | Content (wt %) | |
| Example 16 | Ester of Ex. 1 | 5 | 0.44 |
| Example 17 | Ester of Ex. 2 | 5 | 0.44 |
| Comp. Ex. 9 | — | — | 0.59 |

It is apparent from Table 2 that the additives for the lubricant of the present invention are also excellent in anti-wear properties.

EXAMPLE 18

In a 1-liter flask were placed 262 g (1.0 mol) of p-dodecylphenol (a reaction product of propylene oligomer and phenol) and 262 g of xylene, and they were stirred to be uniformly mixed. Afterward, the mixture was heated up to 70° C., and 80 g of a 48 wt % aqueous sodium hydroxide solution was added thereto. Next, xylene was refluxed under nitrogen gas stream for 2 hours to distill off water. The reaction solution was transferred to a 1-liter autoclave, and it was then pressurized to 10 kg/cm²G by carbon dioxide and reaction was carried out at 155° C. for 1 hour. Next, the temperature of the reaction system was lowered to 80° C., and the solution was then transferred to a 1-liter flask, followed by stirring.

Afterward, 250 g of a 20 wt % aqueous sulfuric acid solution was added dropwise thereto over 30 minutes, and reaction was then done for 1 hour. The resultant reaction solution was washed with water, and after phase separation and filtration, xylene was distilled off. The yield of the resultant reaction product was 257 g. This product was further purified to obtain 5-dodecylsalicylic acid.

In a 500-milliliter flask were placed 110 g of 5-dodecylsalicylic acid and 100 g of dodecylcatecol (a reaction product of propylene oligomer and catechol), and reaction was then carried out at 250° C. for 5 hours. Next, produced water and unreacted materials were distilled off under reduced pressure.

The resultant product contained as a main component a compound represented by the following formula (XXIX):

Formula (XXIX): (5-dodecyl-2-hydroxybenzoic acid) dodecyl-2-hydroxyphenyl ester

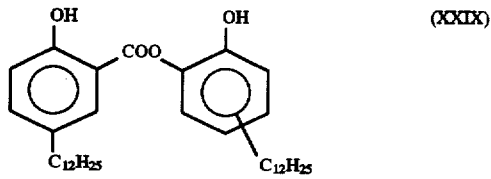

EXAMPLE 19

The same procedure as in Example 18 was carried out except that p-dodecylphenol was replaced with dodecylcatechol.

The resultant product contained as a main component a compound represented by the following formula (XXX):

Formula (XXX): (dodecyl-2,3-dihydroxybenzoic acid) dodecyl-2-hydroxyphenyl ester (XXX)

OH    OH
HO    COO
 \   /    \  /
  [ring]   [ring]
   |         |
  $C_{12}H_{25}$  $C_{12}H_{25}$

EXAMPLE 20

The same procedure as in Example 18 was carried out except that p-dodecylphenol was replaced with 4-dodecyl-1-naphthol and dodecylcatechol was replaced with p-dodecylphenol.

The resultant product contained as a main component a compound represented by the following formula (XXXI):

Formula (XXXI): (4-dodecyl-1-hydroxy-2-naphthoic acid) 4-dodecylphenyl ester

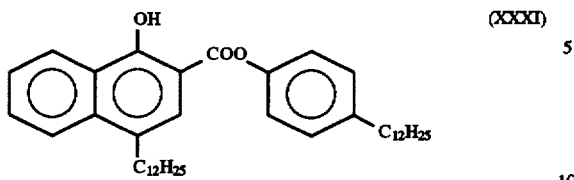

EXAMPLES 21 to 23

Preparation of additive compositions for lubricants (ashless detergent dispersants)

75 wt % of an ashless dispersant (boric acid-treated polybutenylsuccinimide) obtained in Reference Example 1 was blended with 25 wt % of each of substituted hydroxyaromatic ester derivatives obtained in Examples 18 to 20 to prepare additive compositions for lubricants.

EXAMPLES 24 to 26

Preparation of lubricating oil compositions

Each of additive compositions for lubricants obtained in Examples 21 to 23 was blended with a mineral oil which was a 500 neutral fraction to prepare lubricating oil compositions, and in this case, the amount of the additive composition for the lubricant was 10 wt % (2.5 wt % of a substituted hydroxyaromatic ester and 7.5 wt % of an ashless dispersant) based on the total weight of each lubricating oil composition.

The performance of each lubricating oil composition was evaluated in accordance with the same hot tube test as in Examples 11 to 15. The results are shown in Table 3.

|  | Kind of Contained Detergent | Hot Tube Test Grade | Deposit (mg) |
| --- | --- | --- | --- |
| Example 24 | Ester of Ex. 18 | 8 | 1> |
| Example 25 | Ester of Ex. 19 | 8 | 1> |
| Example 26 | Ester of Ex. 20 | 6 | 1> |

The temperature of the hot tube test = 310° C.

EXAMPLE 27

All the same procedure as in Example 1 was carried out to obtain 195 g of a mixture of compounds represented by the general formulae (XIV) and (XV). As a result of liquid chromatograph analysis (a detector=a differential refractometer), a ratio between the compounds represented by the formulae (XIV) and (XV) was the compound of the formula (XIV):the compound of the formula (XV)=78 area %:22 area %.

Next, from this mixture, there were separated (hexadecylsalicylic acid) hexadecylphenyl ester represented by the formula (XIV) and (hexadecylhydroxybenzenedicarboxylic acid) bis (hexadecylphenyl) ester represented by the formula (XV) by liquid chromatograph.

Figure 2:
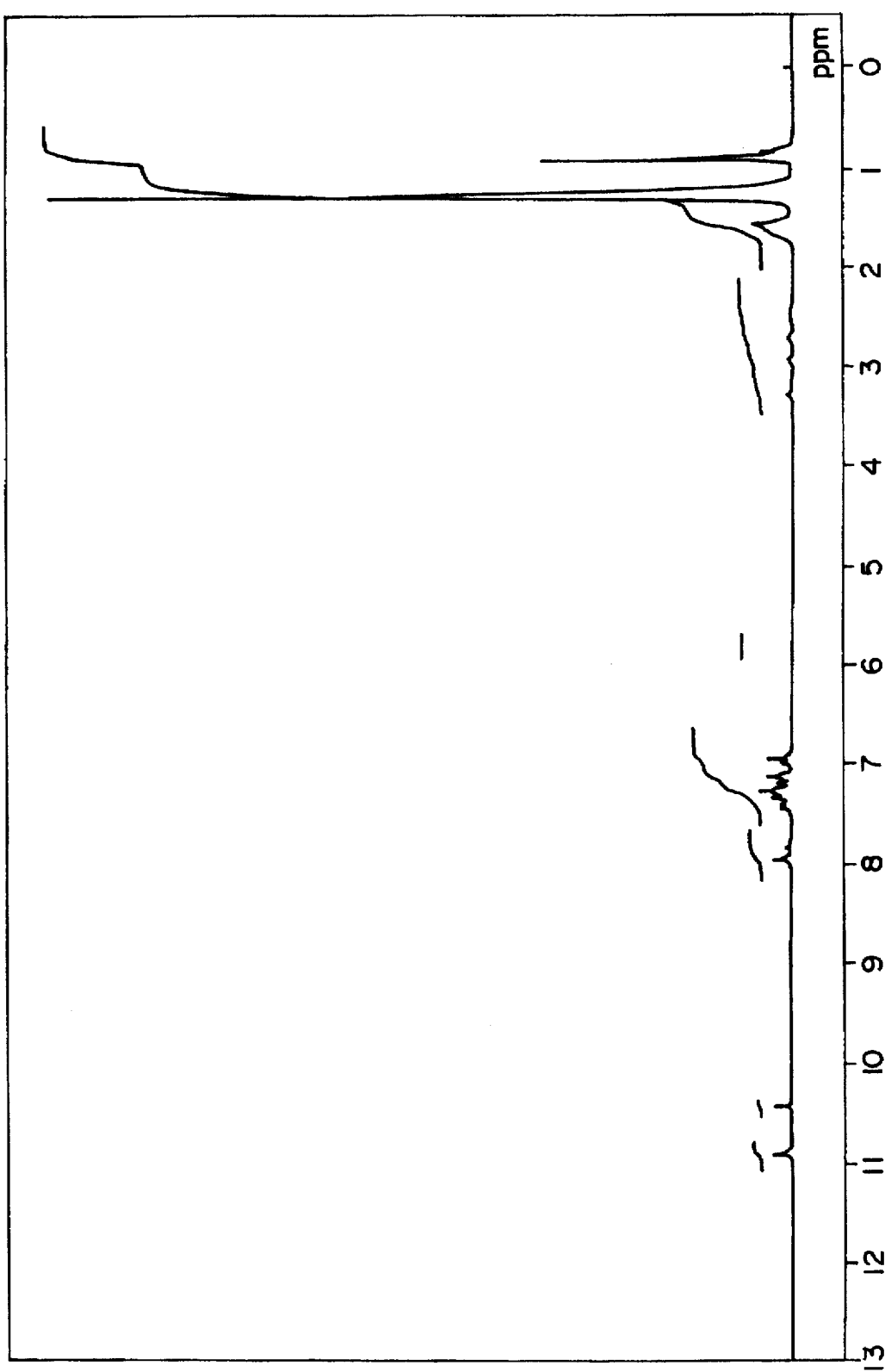
Figure 3:
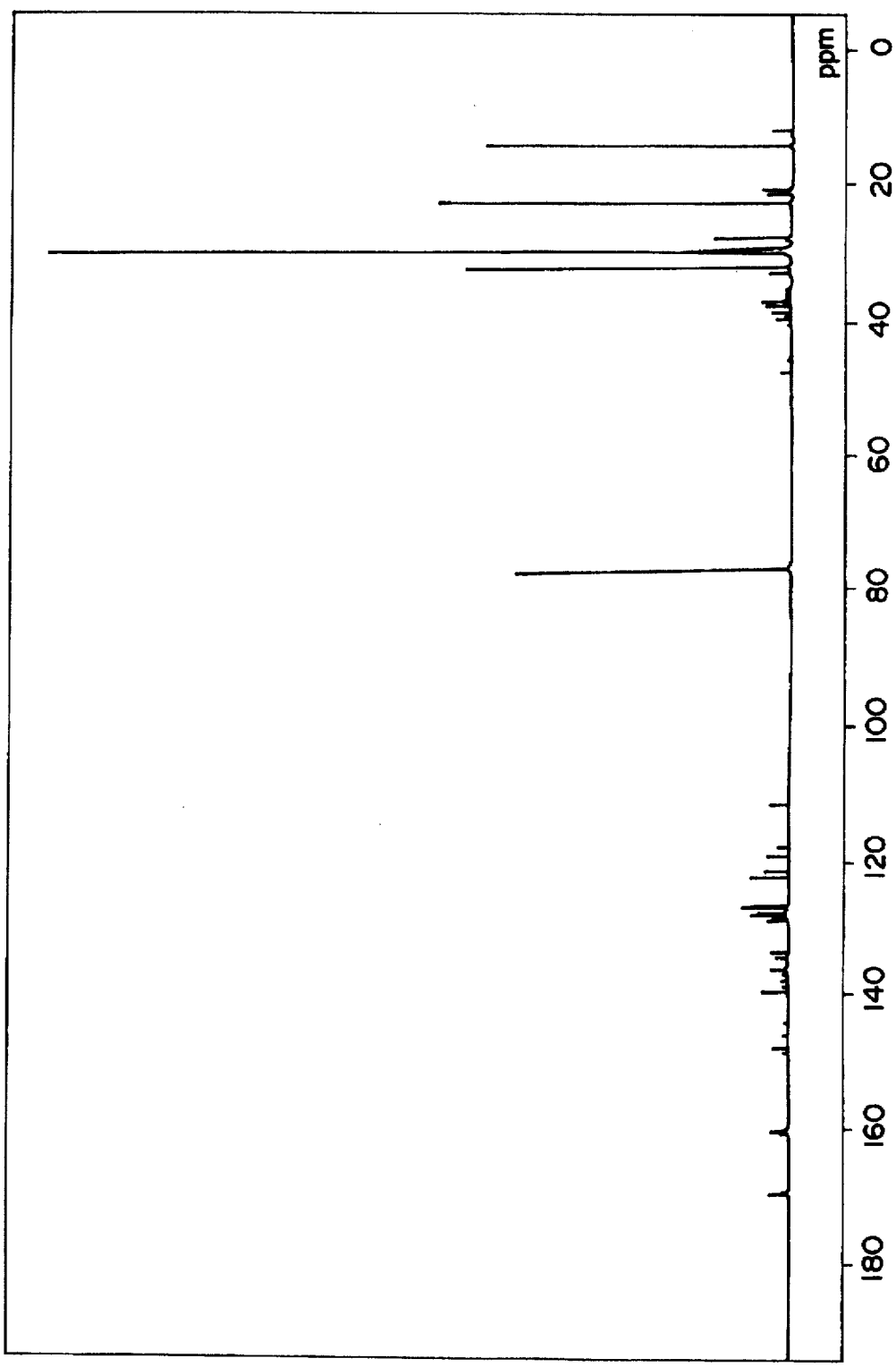

The results of electrolytic desorption ionization mass analysis, proton nuclear magnetic resonance spectroscopy and $^{13}C$ nuclear magnetic resonance spectroscopy of the compound represented by the formula (XIV) are shown in FIGS. 1, 2 and 3, respectively.

Figure 4:
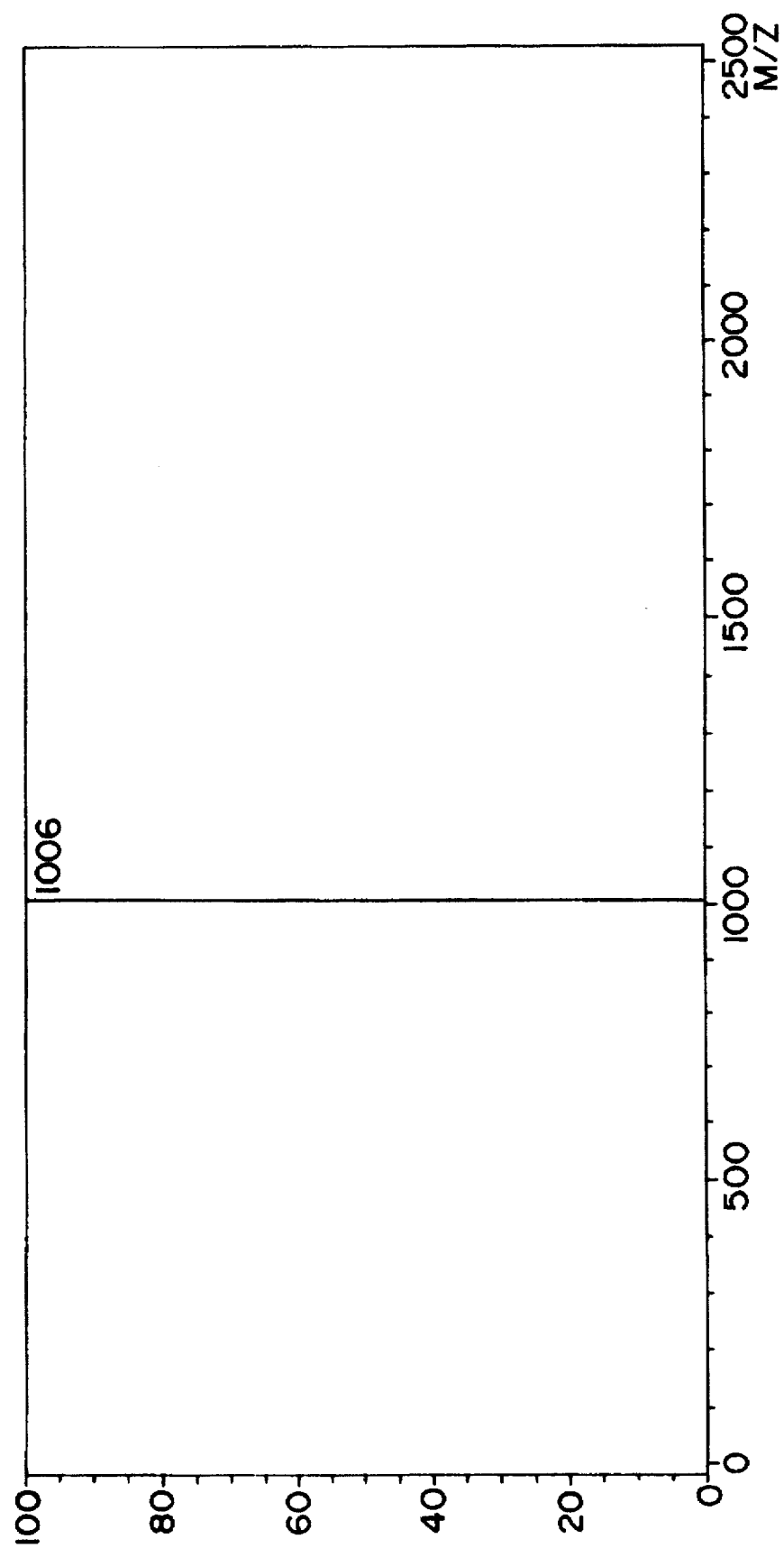
FIGS. 4, 5 and 6 are charts showing the results of the electrolytic desorption ionization mass analysis, proton nuclear magnetic resonance spectroscopy and $^{13}C$ nuclear magnetic resonance spectroscopy of (hexadecylhydroxybenzenedicarboxylic acid) bis(hexadecylphenyl) ester obtained in Example 27, respectively.
Figure 5:
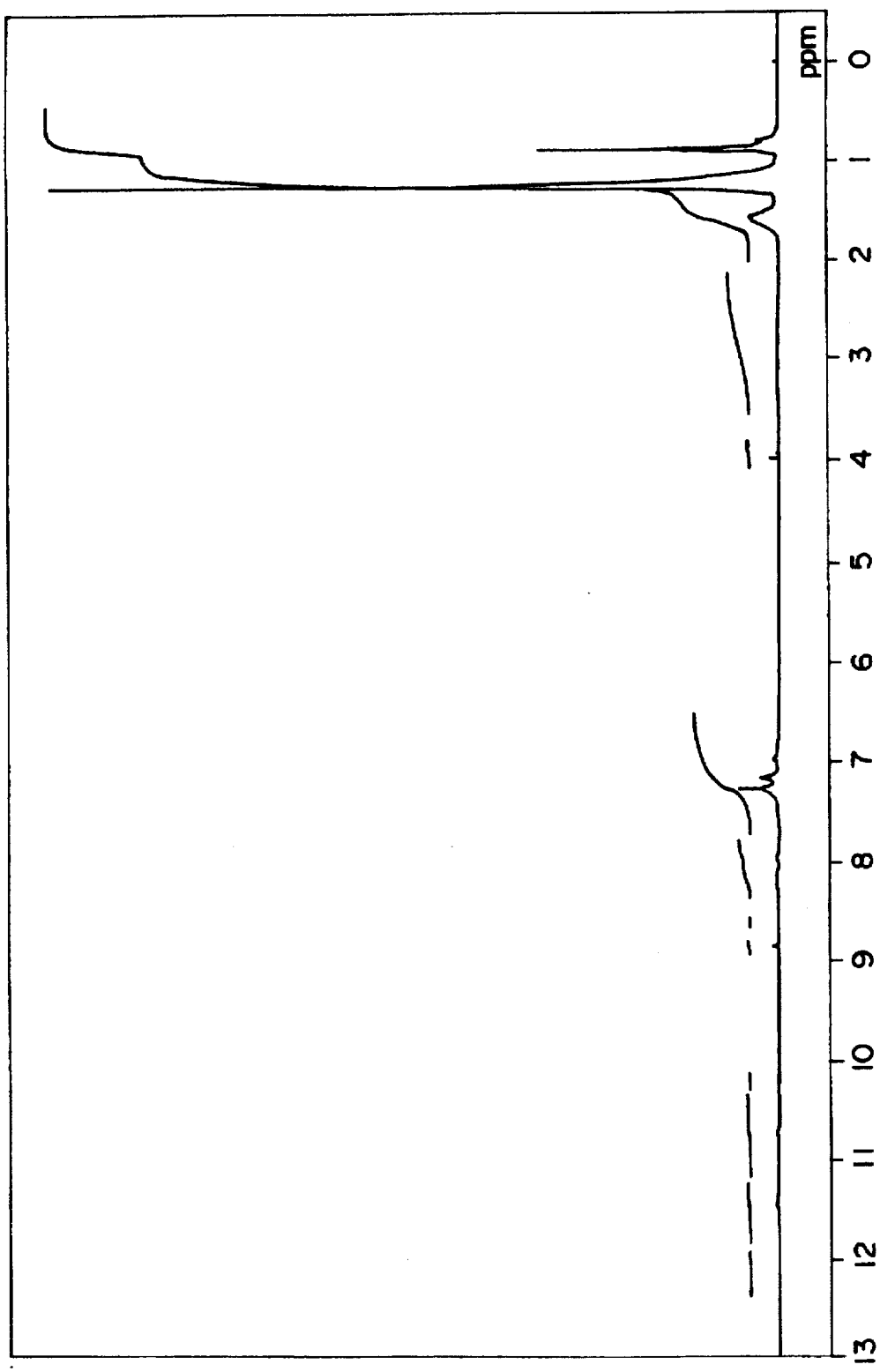
Figure 6:
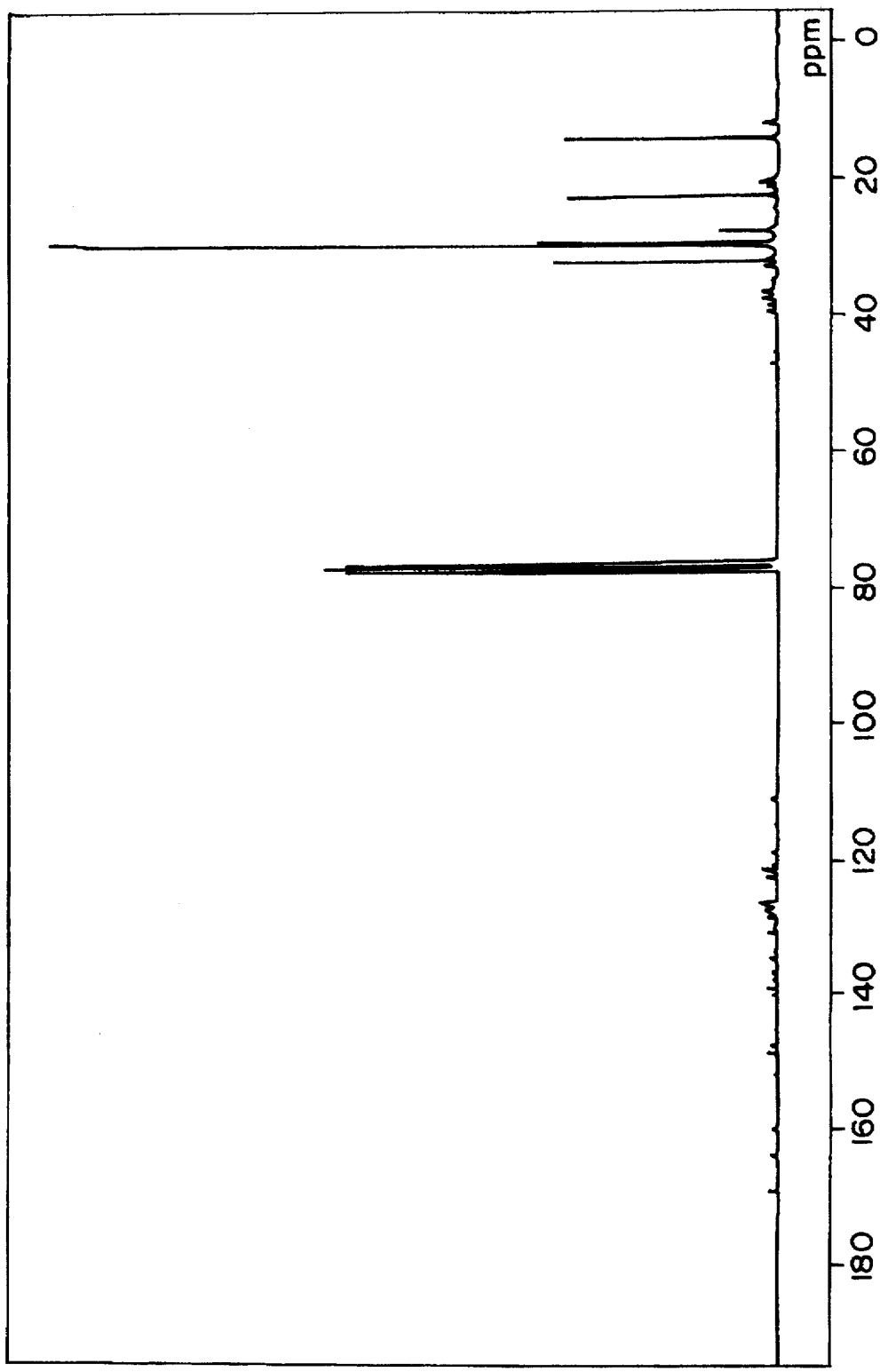

Furthermore, the results of electrolytic desorption ionization mass analysis, proton nuclear magnetic resonance spectroscopy and $^{13}C$ nuclear magnetic resonance spectroscopy of the compound represented by the formula (XV) are shown in FIGS. 4, 5 and 6, respectively.

EXAMPLE 28

The same procedure as in Example 1 was carried out except that hexadecylphenyl was replaced with mixed alkylphenols in which alkyl groups had 11, 12, 13, 14 and 15 carbon atoms (a reaction product of propylene oligomer and phenol).

From the resultant product, mixed compounds represented by the formula (XXXII) and mixed compounds represented by the formula (XXXIII) were separated by liquid chromatograph (in the formulae, R is an alkyl group having 11 to 15 carbon atoms):

Formula (XXXII): (mixed $C_{11}$–$C_{15}$ alkylsalicylic acid) mixed $C_{11}$–$C_{15}$ alkylphenyl esters

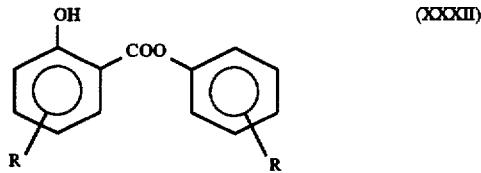

Formula (XXXIII): (mixed $C_{11}$–$C_{15}$ alkylhydroxybenzenedicarboxylic acid) bis(mixed $C_{11}$–$C_{15}$ alkylphenyl) esters

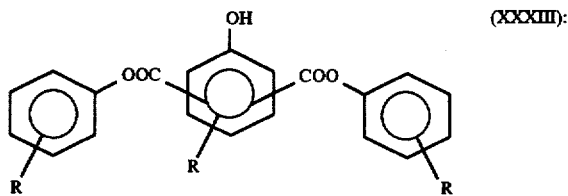

Figure 7:
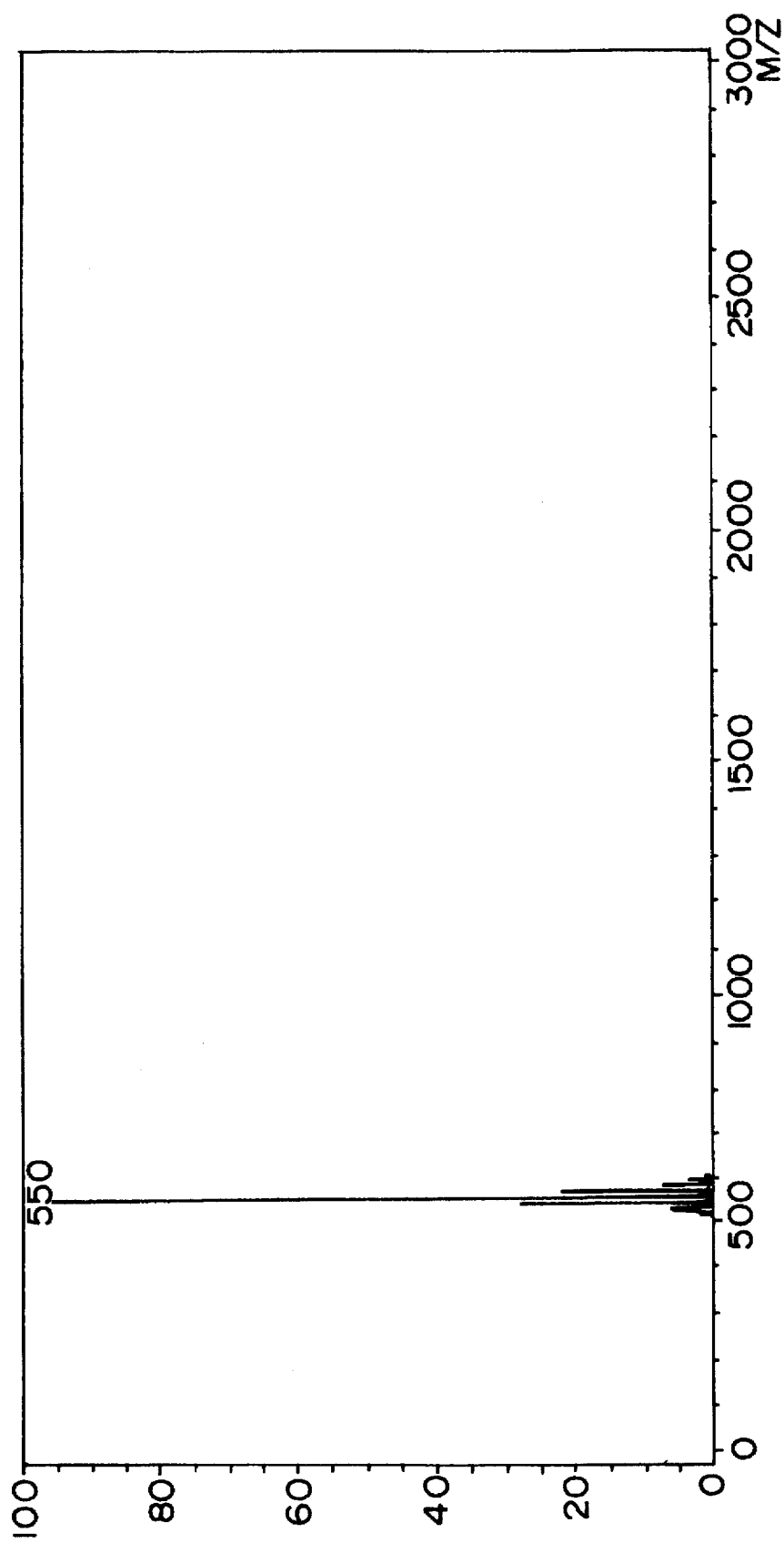
FIG. 7 is a chart showing the results of the electrolytic desorption ionization mass analysis of (mixed $C_{11}$–$C_{15}$ alkylsalicylic acid) mixed $C_{11}$–$C_{15}$ alkylphenyl esters obtained in Example 28.
Figure 8:
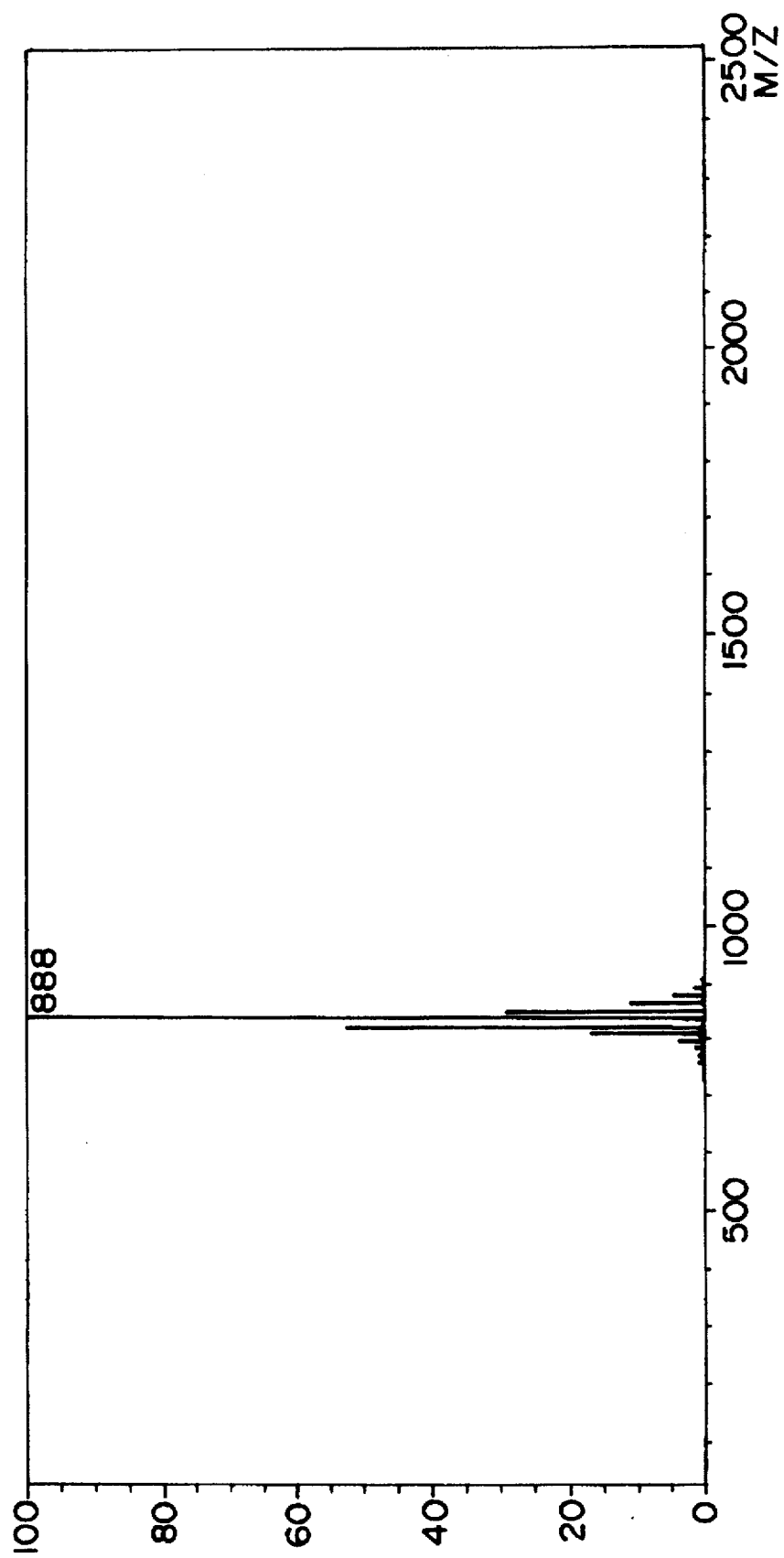
FIG. 8 is a chart showing the results of the electrolytic desorption ionization mass analysis of (mixed $C_{11}$–$C_{15}$ alkylhydroxybenzenedicarboxylic acid) bis(mixed $C_{11}$–$C_{15}$ alkylphenyl) esters obtained in Example 28.

The results of the electrolytic desorption ionization mass analysis of the mixture represented by the formula (XXXII) are shown in FIG. 7, and the results of the electrolytic desorption ionization mass analysis of the mixture represented by the formula (XXXIII) are shown in FIG. 8.

EXAMPLE 29

All the same procedure as in Example 4 was carried out to obtain a mixture of compounds represented by the general formulae (XX) and (XXI).

Next, from this mixture, (5-nonylsalicylic acid) p-nonylphenyl ester represented by the formula (XX) and (5-nonyl-2-hydroxy-1,3-benzenedicarboxylic acid) bis(p-nonylphenyl) ester represented by the formula (XXI) were separated by liquid chromatograph.

Figure 9:
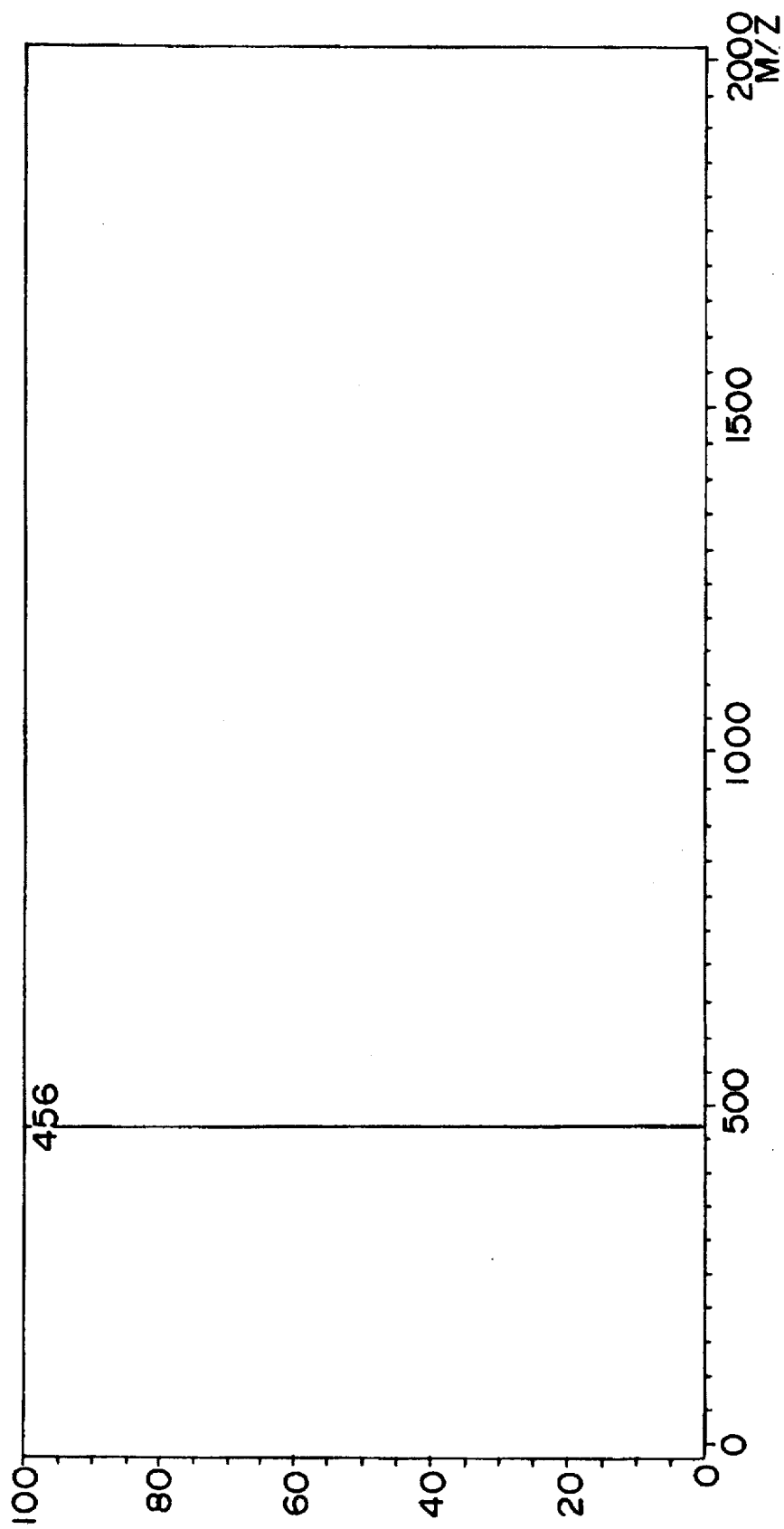
FIGS. 9, 10 and 11 are charts showing the results of the electrolytic desorption ionization mass analysis, proton nuclear magnetic resonance spectroscopy and $^{13}C$ nuclear magnetic resonance spectroscopy of (5-nonyl-salicylic acid) p-nonylphenyl ester obtained in Example 29, respectively.
Figure 10:
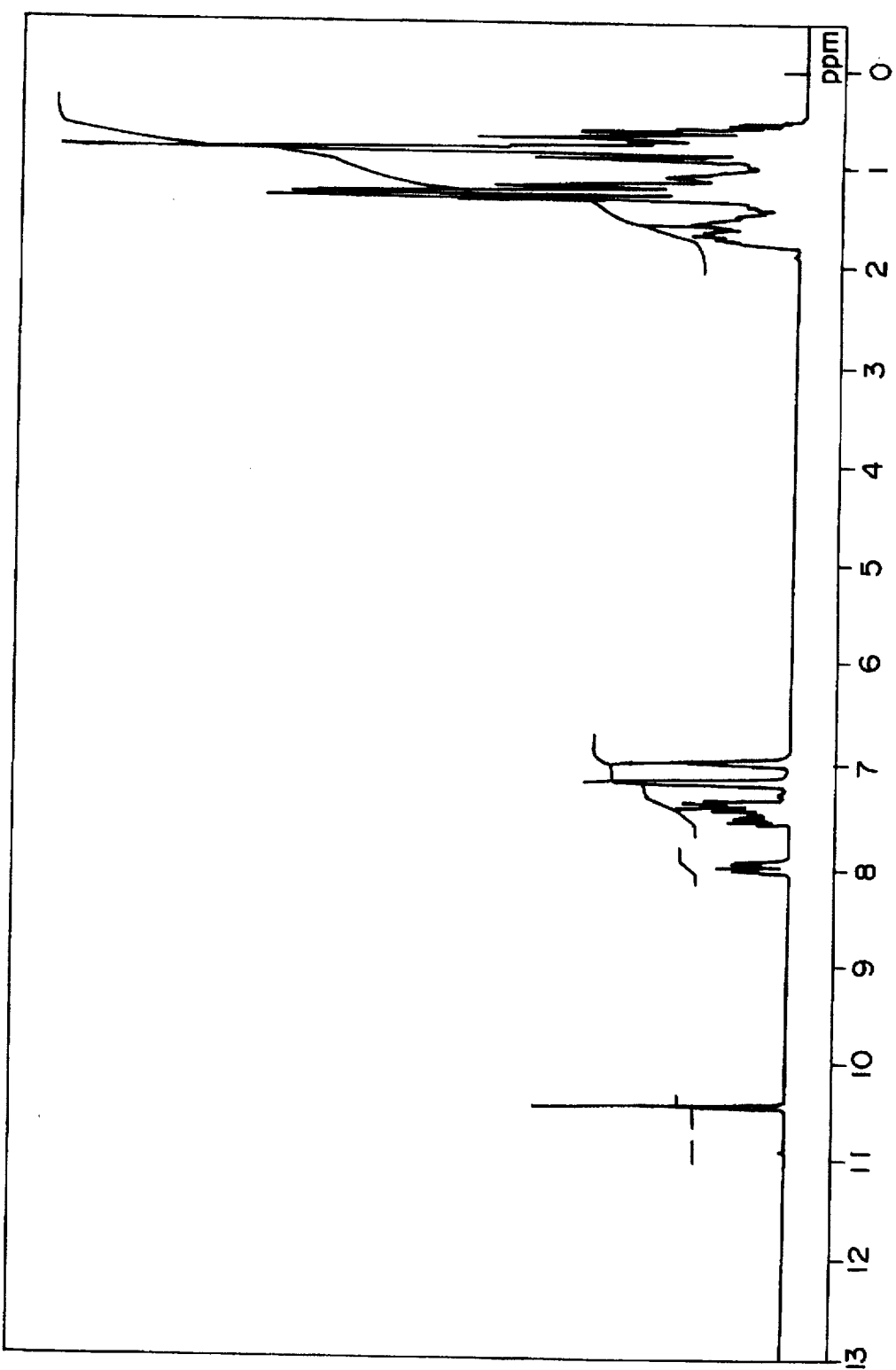
Figure 11:
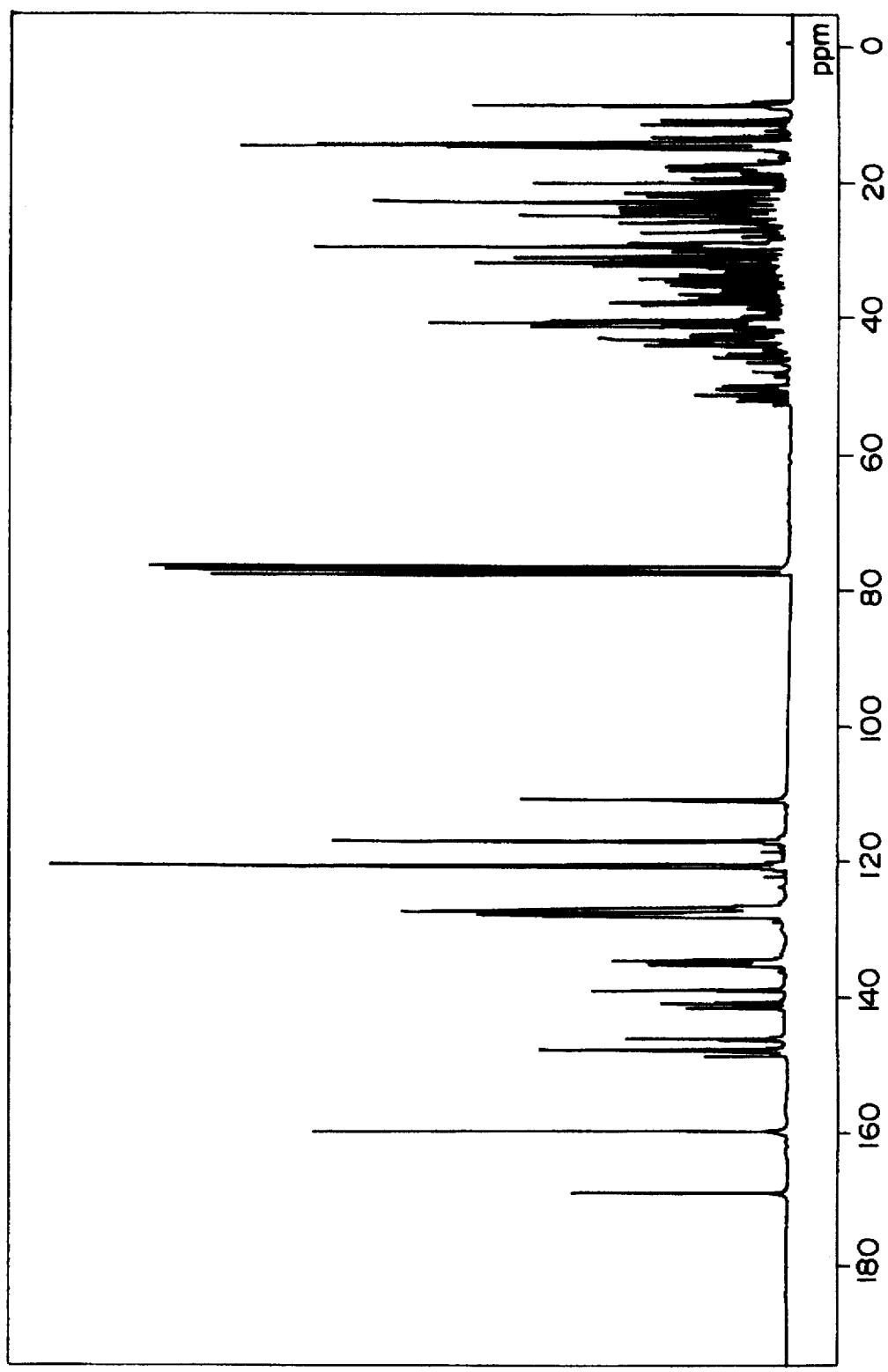

The results of electrolytic desorption ionization mass analysis, proton nuclear magnetic resonance spectroscopy and $^{13}C$ nuclear magnetic resonance spectroscopy of the compound represented by the formula (XX) are shown in FIGS. 9, 10 and 11, respectively.

Figure 12:
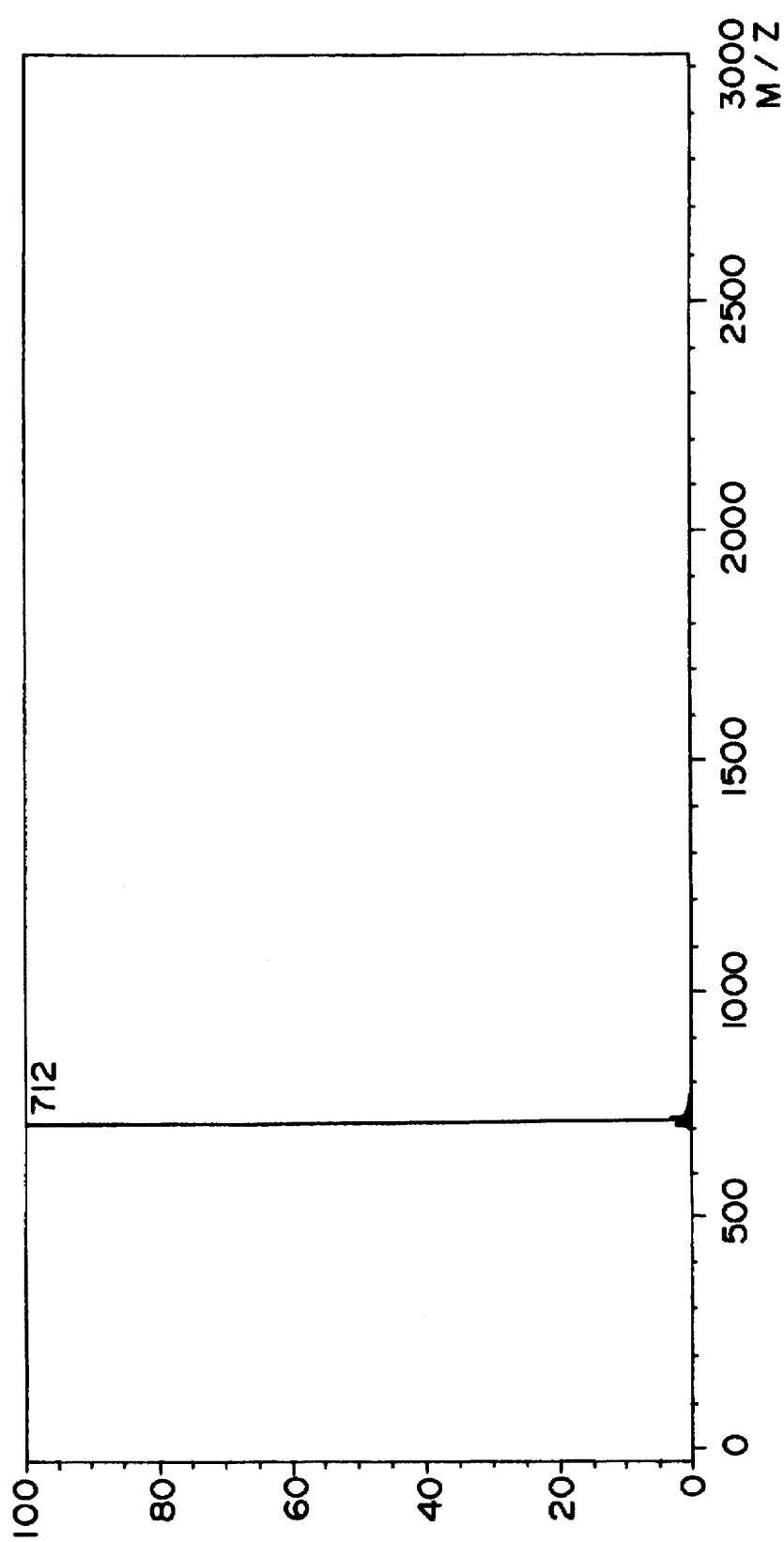
FIGS. 12, 13 and 14 are charts showing the results of the electrolytic desorption ionization mass analysis, proton nuclear magnetic resonance spectroscopy and $^{13}C$ nuclear magnetic resonance spectroscopy of (5-nonyl-2-hydroxy-1, 3-benzenedicarboxylic acid) bis(p-nonylphenyl) ester obtained in Example 29, respectively.
Figure 13:
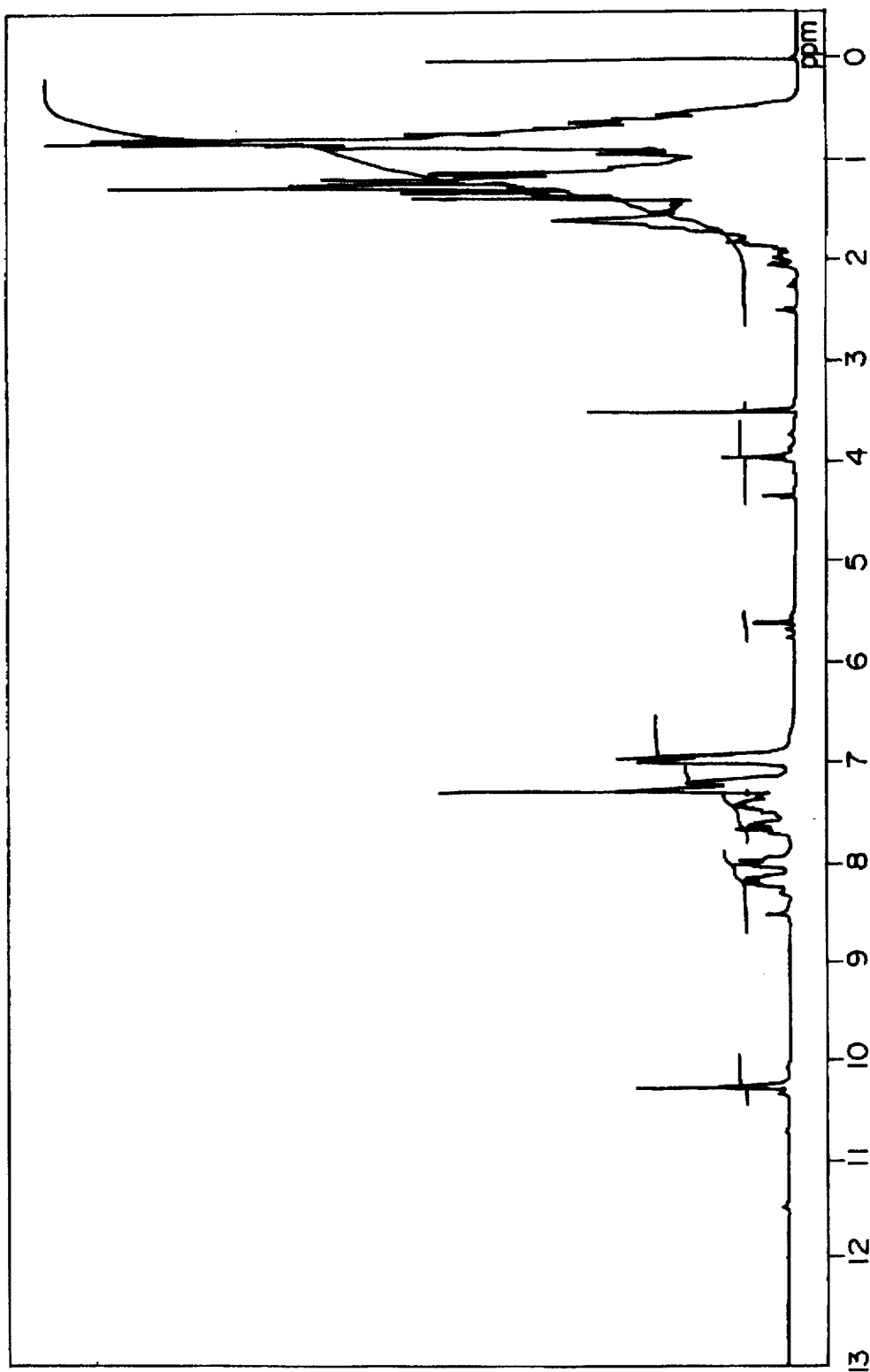
Figure 14:
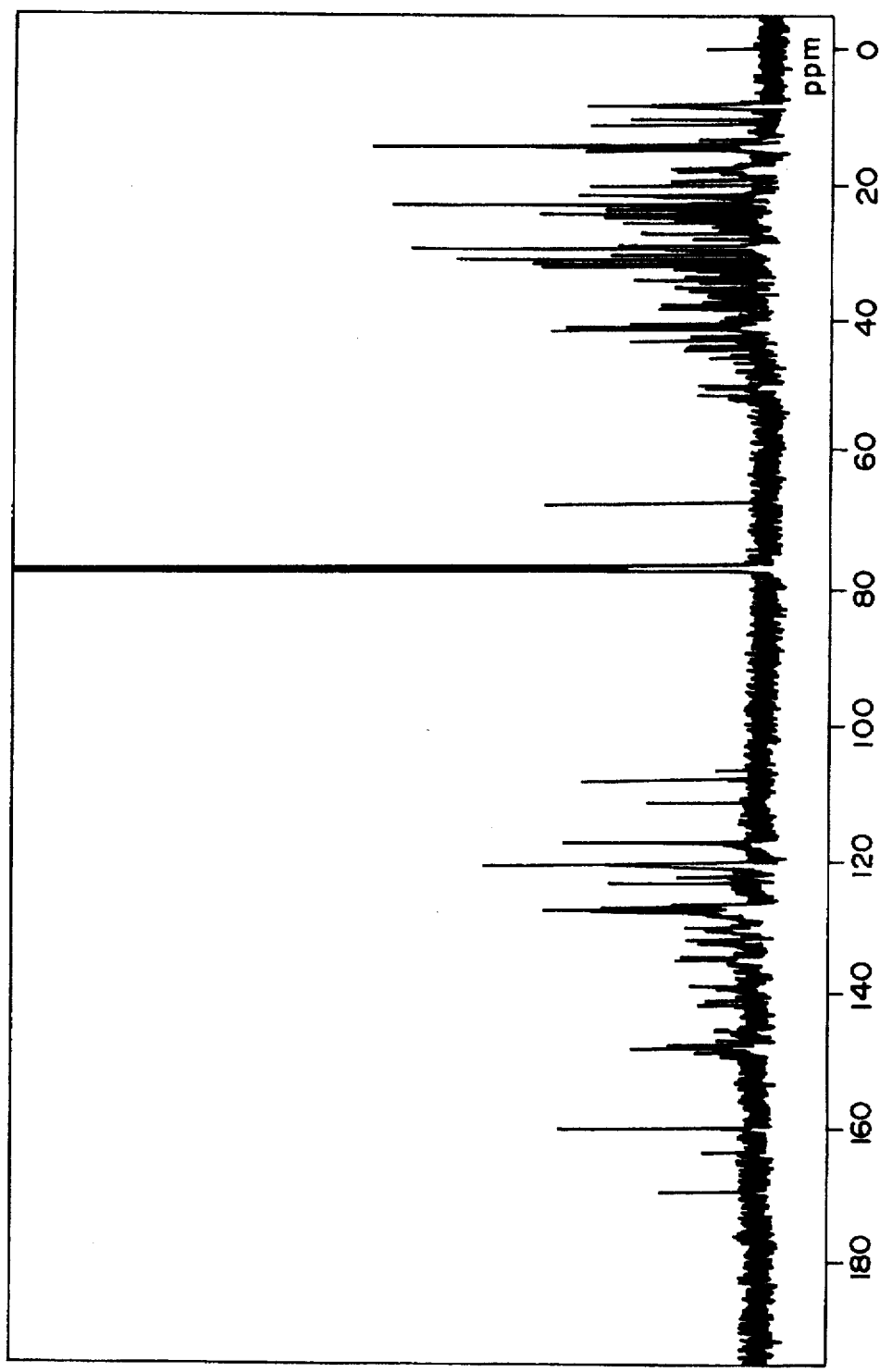

Furthermore, the results of electrolytic desorption ionization mass analysis, proton nuclear magnetic resonance spectroscopy and $^{13}C$ nuclear magnetic resonance spectroscopy of the compound represented by the formula (XXI) are shown in FIGS. 12, 13 and 14, respectively.

EXAMPLES 30 to 32

(1) Preparation of additive compositions for lubricants (ashless detergent dispersants)

75 wt % of an ashless dispersant (boric acid-treated polybutenylsuccinimide) obtained in Reference Example 1 was blended with 25 wt % of each of substituted hydroxyaromatic ester derivatives represented by the formulae (XIV), (XXXII) and (XX) obtained in Examples 27 to 29 to prepare additive compositions for lubricants.

(2) Preparation of lubricating oil compositions

Each of the additive compositions for the lubricants obtained in the above-mentioned (1) was blended with a mineral oil which was a 500 neutral fraction to prepare lubricating oil compositions, and in this case, the amount of the additive composition for the lubricant was 10 wt % (2.5 wt % of the substituted hydroxyaromatic ester and 7.5 wt % of the ashless dispersant) based on the total weight of each lubricating oil composition.

The performance of the lubricating oil compositions was evaluated in accordance with the same hot tube test as in Examples 11 to 15. The results are shown in Table 4.

TABLE 4

| | Contained Detergent | | | Hot Tube Test (310° C.) | |
|---|---|---|---|---|---|
| | | Substituent | | | Deposit |
| | Kind | $R^6$ | $R^7$ | Grade | (mg) |
| Example 30 | Ester (XIV) of Ex. 27 | $C_{16}H_{33}$ | $C_{16}H_{33}$ | 8 | 1> |
| Example 31 | Ester (XXXII) of Ex. 28 | $C_{11}H_{23}$ to $C_{15}H_{31}$ | $C_{11}H_{23}$ to $C_{15}H_{31}$ | 8 | 1> |
| Example 32 | Ester (XX) of Ex. 29 | $C_9H_{19}$ | $C_9H_{19}$ | 7 | 1> |

EXAMPLES 33 to 35

(1) Preparation of additive compositions for lubricants (ashless detergent dispersants)

75 wt % of an ashless dispersant (boric acid-treated polybutenylsuccinimide) obtained in Reference Example 1 was blended with 25 wt % of each of substituted hydroxyaromatic ester derivatives represented by the formulae (XV), (XXXIII) and (XXI) obtained in Examples 27 to 29 to prepare additive compositions for lubricants.

(2) Preparation of lubricating oil compositions

Each of the additive compositions for the lubricants obtained in the above-mentioned (1) was blended with a mineral oil which was a 500 neutral fraction to prepare lubricating oil compositions, and in this case, the amount of the additive composition for the lubricant was 10 wt % (2.5 wt % of the substituted hydroxyaromatic ester derivative and 7.5 wt % of the ashless dispersant) based on the total weight of each lubricating oil composition.

The performance of the lubricating oil compositions was evaluated in accordance with the same hot tube test as in Examples 11 to 15. The results are shown in Table 5.

TABLE 5

| | | Hot Tube Test | |
|---|---|---|---|
| | Kind of Contained Detergent | Grade | Deposit (mg) |
| Example 33 | Ester (XV) of Ex. 27 | 8 | 1> |
| Example 34 | Ester (XXXIII) of Ex. 28 | 8 | 1> |
| Example 35 | Ester (XXI) of Ex. 29 | 8 | 1> |

The temperature of the hot tube test = 310° C.

EXAMPLE 36

Preparation of fuel composition

A diesel gas oil (boiling point=180°–350° C.) was blended with a polyoxyethylene compound represented by $C_{16}H_{33}NH(CH_2CH_2O)_6H$ and a substituted hydroxyaromatic ester derivative of Example 1 in amounts of 1 wt % and 0.2 wt %, respectively, based on the total weight of a composition, thereby preparing a diesel gas oil composition.

The performance of this composition was evaluated by the following storage stability test. The results are shown in Table 6.

[Storage stability test]

100 ml of the diesel gas oil composition was sampled in a test tube, and this test tube was sealed with a cork stopper and then allowed to stand for 2 months in a dark place. Afterward, the weight of a formed sludge was measured.

COMPARATIVE EXAMPLE 10

A diesel gas oil was blended with a polyoxyethylene compound used in Example 36 in an amount of 1 wt % based on the total weight of a composition, thereby preparing a diesel gas oil composition. The performance of this composition was evaluated by the same storage stability test as in Example 36. The results are shown in Table 6.

TABLE 6

| | Contained Ester Derivative | | Storage Stability Test |
|---|---|---|---|
| | Kind | Content (wt %) | Sludge Weight (mg/100 ml) |
| Example 36 | Ester of Ex. 1 | 0.2 | 1 or less |
| Comp. Ex. 10 | — | — | 10 |

Possibility of Industrial Utilization

An additive for a lubricant or a fuel which comprises a specific substituted hydroxyaromatic ester derivative of the present invention can be added to an engine oil for an internal combustion engine, a gear oil, a bearing oil, a shock absorber oil and an industrial lubricating oil, or a fuel for the internal combustion engine.

Furthermore, this additive for the lubricant is useful as an excellent ashless dispersant and anti-wear agent. Moreover, an additive composition for the lubricant containing the ashless dispersant is excellent in high-temperature stability (high-temperature detergency) and has a fine particles dispersion function, and therefore it is useful as an excellent ashless detergent dispersant for a lubricating oil. Above all, the additive composition for the lubricant can be added to a diesel engine oil and a methanol engine oil which can comply with future severe exhaust gas controls.

The above-mentioned additive for a fuel is useful as an ashless detergent, as an anti-wear agent for preventing the abrasion of an injection pump which is caused by the drop of a sulfur content in a gas oil, and as a storage stabilizer for a diesel gas oil composition to which a particulate reducer such as a polyoxyethylene compound is added. In addition, an additive composition for a fuel containing the ashless dispersant is excellent in the high-temperature stability (the high-temperature detergency) and has the fine particles dispersion function, and therefore it is useful as an excellent ashless detergent dispersant for a fuel composition. Thus, the additive composition for the fuel can prevent a deposit from adhering to a carburetor or a injector of an internal combustion engine, and it can also remove adhered materials. Therefore, this additive composition for the fuel can be added to gasoline, kerosine, gas oil and the like.

Furthermore, a novel substituted hydroxyaromatic ester derivative of the present invention can similarly be fed to the above-mentioned applications.

We claim:

1. An additive for a lubricant comprising at least one selected from the group consisting of substituted hydroxyaromatic ester derivatives represented by the general formula (I)

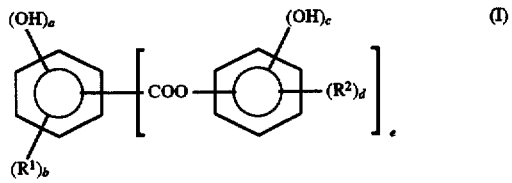

wherein $R^1$ and $R^2$ are each an organic group having 6 or more carbon atoms, and they may be the same or different; a, b, c, d and e are integers satisfying the relations of $1 \leq a \leq 3$, $1 \leq b \leq 3$, $0 \leq c \leq 3$, $1 \leq d \leq 3$, $1 \leq e \leq 3$, $3 \leq (a+b+c) \leq 6$ and $1 \leq (c+d) \leq 5$, respectively; and when a plurality of $R^1$s and $R^2$s are present, they may be the same or different, and the general formula (II)

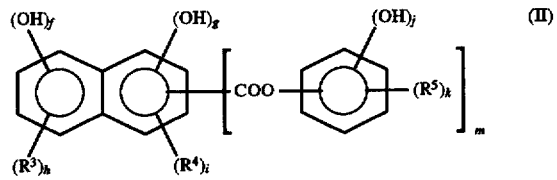

wherein $R^3$, $R^4$ and $R^5$ are each an organic group having 6 or more carbon atoms, and they may be the same or different; f, g, h, i, j, k and m are integers satisfying the relations of $0 \leq f \leq 3$, $0 \leq g \leq 3$, $1 \leq (f+g) \leq 3$, $0 \leq h \leq 4$, $0 \leq i \leq 3$, $1 \leq (h+i) \leq 6$, $0 \leq j \leq 3$, $1 \leq k \leq 3$, $1 \leq m \leq 3$, $3 \leq (f+g+h+i+m) \leq 8$ and $1 \leq (j+K) \leq 5$, respectively; and when a plurality of $R^3$s, $R^4$s and $R^5$s are present, they may be the same or different.

2. The additive for a lubricant according to claim 1 wherein the substituted hydroxyaromatic ester derivative is represented by the general formula (III)

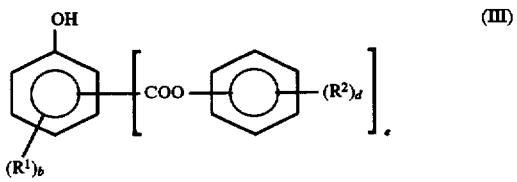

wherein $R^1$ and $R^2$ are each an organic group having 6 or more carbon atom, and they may be the same or different; b, d and e are integers satisfying the relations of $1 \leq b \leq 3$, $1 \leq d \leq 3$, $1 \leq e \leq 3$ and $2 \leq (b+e) \leq 5$, respectively; and when a plurality of $R^1$s and $R^2$s are present, they may be the same or different, or the general formula (III')

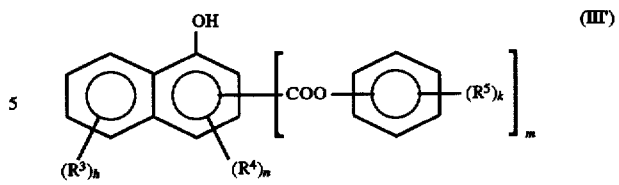

wherein $R^3$, $R^4$ and $R^5$ are each an organic group having 6 or more carbon atoms, and they may be the same or different; h, n, k and m are integers satisfying the relations of $0 \leq h \leq 4$, $0 \leq n \leq 2$, $1 \leq (h+n) \leq 6$, $1 \leq k \leq 3$, $1 \leq m \leq 3$ and $2 \leq (h+n+m) \leq 7$, respectively; and when a plurality of $R^3$s, $R^4$s and $R^5$s are present, they may be the same or different.

3. An additive composition for a lubricant which comprises (a) said additive according to claim 1 which includes said at least one selected from substituted hydroxyaromatic ester derivatives represented by the general formulae (I) and (II), and (b) an ashless dispersant.

4. An additive composition for a lubricant which comprises (a) said additive according to claim 2 which includes at least one selected from the substituted hydroxyaromatic ester derivatives represented by the general formulae (III) and (III') and an ashless dispersant.

5. A lubricant composition which is obtained by adding, to a base oil for a lubricating oil, said additive according to claim 1 which includes said at least one selected from substituted hydroxyaromatic ester derivatives represented by the general formulae (I) and (II).

6. A lubricant composition which is obtained by adding, to a base oil for a lubricant, (a) said additive according to claim 1 which includes said at least one selected from substituted hydroxyaromatic ester derivatives represented by the general formulae (I) and (II), and (b) an ashless dispersant.

7. The lubricant composition according to claim 5 or 6 which is a lubricating oil composition for an internal combustion engine.

8. A lubricant composition which is obtained by adding, to a base oil for a lubricating oil, said additive according to claim 2 which includes said at least one selected from the substituted hydroxyaromatic ester derivatives represented by the general formulae (III) and (III').

9. A lubricant composition which is obtained by adding, to a base oil for a lubricating oil, (a) said additive according to claim 2 which includes said at least one selected from the substituted hydroxyaromatic ester derivatives represented by the general formulae (III) and (III'), and (b) an ashless dispersant.

10. The additive for a lubricant according to claim 1, including at least one selected from the group consisting of substituted hydroxyaromatic esters represented by the general formula (II).

11. The additive for a lubricant according to claim 2, wherein the substituted hydroxyaromatic ester derivative is represented by the general formula (III').

12. An additive composition for a lubricant which comprises (a) said additive according to claim 10 or 11, and (b) an ashless dispersant.

13. A lubricant composition for a lubricant which is obtained by adding, to a base oil for a lubricant, said additive according to claim 10 or 11.

14. A lubricant composition for a lubricant which is obtained by adding, to a base oil for a lubricant, (a) said additive according to claim 10 or 11, and (b) an ashless dispersant.

15. An additive for a fuel which comprises at least one selected from the group consisting of substituted hydroxyaromatic ester derivatives represented by the general formula (I)

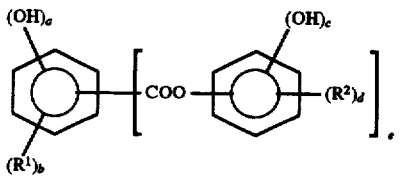

wherein $R^1$ and $R^2$ are each an organic group having 6 or more carbon atoms, and they may be the same or different; a, b, c, d and e are integers satisfying the relations of $1 \leq a \leq 3$, $1 \leq b \leq 3$, $0 \leq c \leq 3$, $1 \leq d \leq 3$, $1 \leq e \leq 3$, $3 \leq (a+b+e) \leq 6$ and $1 \leq (c+d) \leq 5$, respectively; and when a plurality of $R^1$s and $R^2$s are present, they may be the same or different, and the general formula (II)

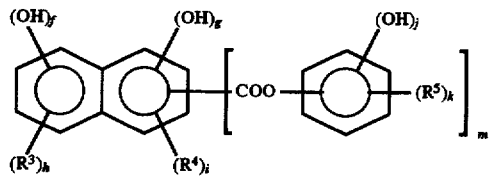

wherein $R^3$, $R^4$ and $R^5$ are each an organic group having 6 or more carbon atoms, and they may be the same or different; f, g, h, i, j, k and m are integers satisfying the relations of $0 \leq f \leq 3$, $0 \leq g \leq 3$, $1 \leq (f+g) \leq 3$, $0 \leq h \leq 4$, $0 \leq i \leq 3$, $1 \leq (h+i) \leq 6$, $0 \leq j \leq 3$, $1 \leq k \leq 3$, $1 \leq m \leq 3$, $3 \leq (f+g+h+i+m) \leq 8$ and $1 \leq (j+K) \leq 5$, respectively; and when a plurality of $R^3$s, $R^4$s and $R^5$s are present, they may be the same or different.

16. The additive for a fuel according to claim 15 wherein the substituted hydroxyaromatic ester derivative represented by the general formula (III)

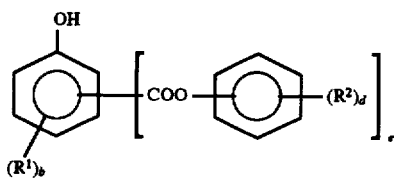

wherein $R^1$ and $R^2$ are each an organic group having 6 or more carbon atoms, and they may be the same or different; b, d and e are integers satisfying the relations of $1 \leq b \leq 3$, $1 \leq d \leq 3$, $1 \leq e \leq 3$ and $2 \leq (b+e) \leq 5$, respectively; and when a plurality of $R^1$s and $R^2$s are present, they may be the same or different, or the general formula (III')

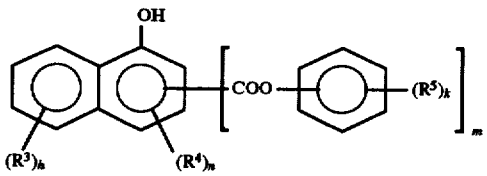

wherein $R^3$, $R^4$ and $R^5$ are each an organic group having 6 or more carbon atoms, and they may be the same or different; h, n, k and m are integers satisfying the relations of $0 \leq h \leq 4$, $0 \leq n \leq 2$, $1 \leq (h+n) \leq 6$, $1 \leq k \leq 3$, $1 \leq m \leq 3$ and $2 \leq (h+n+m) \leq 7$, respectively; and when a plurality of $R^3$s, $R^4$s and $R^5$s are present, they may be the same or different.

17. An additive composition for a fuel which comprises (a) said additive according to claim 15 which includes said at least one selected from substituted hydroxyaromatic ester derivatives represented by the general formulae (I) and (II), and (b) an ashless dispersant.

18. An additive composition for a fuel which comprises (a) said additive according to claim 16 which includes at least one selected from the substituted hydroxyaromatic ester derivatives represented by the general formula (III) add (III'), and (b) an ashless dispersant.

19. A fuel composition which is obtained by adding, to a fuel, said additive according to claim 15 which includes said at least one selected from substituted hydroxyaromatic ester derivatives represented by the general formulae (I) and (II).

20. A fuel composition which is obtained by adding, to a fuel, (a) said additive according to claim 15 which includes said at least one selected from substituted hydroxyaromatic ester derivatives represented by the general formulae (I) and (II), and (b) an ashless dispersant.

21. The fuel composition according to claim 19 or 20 which is a fuel composition for an internal combustion engine.

22. A fuel composition which is obtained by adding, to a fuel, said additive according to claim 16 which includes said at least one selected from the substituted hydroxyaromatic ester derivatives represented by the general formulae (III) and (III').

23. A fuel composition which is obtained by adding, to a fuel, (a) said additive according to claim 16 which includes said at least one selected from the substituted hydroxyaromatic ester derivatives represented by the general formulae (III) and (III'), and (b) an ashless dispersant.

24. The additive for a fuel according to claim 15, including at least one selected from the group consisting of substituted hydroxyaromatic esters represented by the general formula (II).

25. The additive for a fuel according to claim 16, wherein the substituted hydroxyaromatic ester derivative is represented by the general formula (III').

26. An additive composition for a fuel which comprises (a) said additive according to claim 24 or 25 and (b) an ashless dispersant.

27. A fuel composition which is obtained by adding, to a fuel, said additive according to claim 24 or 25.

28. A fuel composition which is obtained by adding, to a fuel, (a) said additive according to claim 24 or 25, and (b) an ashless dispersant.

29. A substituted hydroxyaromatic ester derivative represented by the general formula (IV)

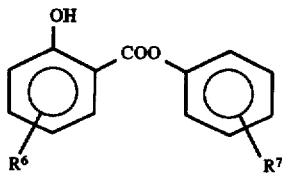

wherein $R^6$ and $R^7$ are each an alkyl group having 9 to 20 carbon atoms, and they may be the same or different.

30. A process for preparing a substituted hydroxyaromatic ester derivative described in claim 29 which comprises the step of reacting an alkyl group-substituted salicylic acid represented by the general formula (V)

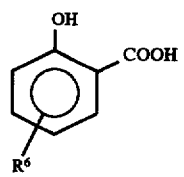

wherein $R^6$ is an alkyl group having 9 to 20 carbon atoms, with an alkyl-substituted phenol represented by the general formula (VI)

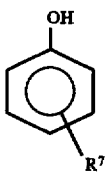
(VI)

wherein $R^7$ is an alkyl group having 9 to 20 carbon atoms, in the presence of no catalyst or a catalyst.

31. A substituted hydroxyaromatic ester derivative represented by the general formula (VII)

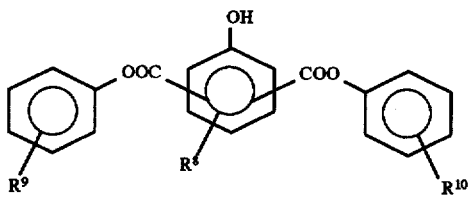
(VII)

wherein $R^8$, $R^9$ and $R^{10}$ are each a hydrocarbon group, and they may be the same or different.

32. The substituted hydroxyaromatic ester derivative according to claims 31 wherein $R^8$ of the general formula (VII) is an alkyl group.

33. A process for preparing a substituted hydroxyaromatic ester derivative described in claim 31 which comprises the step of reacting a hydrocarbon group-substituted hydroxybenzenedicarboxylic acid represented by the general formula (VIII)

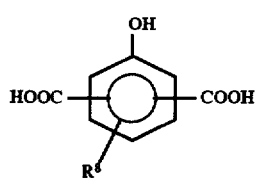
(VIII)

wherein $R^8$ is a hydrocarbon group, with at least one of hydrocarbon group-substituted phenols represented by the general formula (IX)

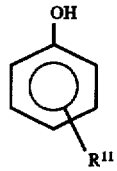
(IX)

wherein $R^{11}$ is $R^9$ or $R^{10}$, and it is a hydrocarbon group, in the presence of no catalyst or a catalyst.

34. The process for preparing a substituted hydroxyaromatic ester derivative according to claim 33 wherein $R^8$ of the general formula (VIII) is an alkyl group.

* * * * *